(12) United States Patent
Nemoto et al.

(10) Patent No.: US 12,152,086 B2
(45) Date of Patent: Nov. 26, 2024

(54) LIPOSOME BINDING PEPTIDE, CONSTRUCT FOR MANUFACTURING THE LIPOSOME BINDING PEPTIDE, AND LIPOSOME

(71) Applicant: Saitama University, Saitama (JP)

(72) Inventors: Naoto Nemoto, Saitama (JP); Yasuhito Utsugi, Saitama (JP)

(73) Assignees: Saitama University, Saitama (JP); Epsilon Molecular Engineering Incorporated, Saitama (JP)

( * ) Notice: Subject to any disclaimer, the term of this patent is extended or adjusted under 35 U.S.C. 154(b) by 777 days.

(21) Appl. No.: 17/315,041

(22) Filed: May 7, 2021

(65) Prior Publication Data

US 2021/0403604 A1 Dec. 30, 2021

Related U.S. Application Data

(63) Continuation of application No. PCT/JP2019/043771, filed on Nov. 7, 2019.

(30) Foreign Application Priority Data

Nov. 8, 2018 (JP) ................. 2018-210873

(51) Int. Cl.
C07K 17/04 (2006.01)
C07K 7/06 (2006.01)

(52) U.S. Cl.
CPC .............. *C07K 17/04* (2013.01); *C07K 7/06* (2013.01)

(58) Field of Classification Search
None
See application file for complete search history.

(56) References Cited

U.S. PATENT DOCUMENTS

2017/0209537 A1 7/2017 Anantharamaiah et al.

FOREIGN PATENT DOCUMENTS

JP 2015-067578 A 4/2015
WO 2016/018665 A1 2/2016

OTHER PUBLICATIONS

Office Action dated Jan. 4, 2023, issued for the corresponding Singapore Patent Application No. 11202104819Y.

Kobayashi, S, et al., "In vitro selection of random peptides against artificial lipid bilayers: a potential tool to immobilize molecules on membranes", ChemComm, 2017, vol. 53, pp. 3458-3461. (cited in the ISR; discussed in the spec).

Ohkawa, Ryoya et al., "Liposome binding peptide sequences to immobilize proteins on a liposome easily", The Molecular Biology Society of Japan, The 39th Annual Meeting of the Molecular Biology Society of Japan, 2016, [2P-0821], lines 11-17. (cited in the ISR).

Miyajima, H. et al., "High-throughput Selection of Pore-forming Peptides Assembling in Liposome Membranes by Combining cDNA Display Method with Cell Sorter System", Peptide Science 2017 Proceedings of the 54th Japanese Peptide Symposium, Jun. 1, 2018 (accession date), pp. 30-31. (cited in the ISR).

Utsugi, Yasuhito et al., "Liposomal membrane permeation by a novel peptide fusion protein", The Molecular Biology Society of Japan, The 41st annual conference of the Molecular Biology Society of Japan, 2018, 3P-0745, entire text, non-official translation. (cited in the ISR).

Maria S. Zharkova et al., "Application of Antimicrobial Peptides of the Innate Immune System in Combination With Conventional Antibiotics—A Novel Way to Combat Antibiotic Resistance?" Frontiers in Cellular and Infection Microbiology, vol. 9 Article128, Apr. 2019, pp. 1-23. (discussed in the spec).

Amr Selim Abu Lila et al., "Liposomal Delivery Systems: Design Optimization and Current Applications," The Pharmaceutical Society of Japan, Biol. Pharm. Bull., vol. 40, No. 1, 2017, pp. 1-10. (discussed in the spec).

Office Action mailed Feb. 28, 2023, issued for Japanese Patent Application No. 2020-555607 and English translation thereof.

Utsugi, Yasuhito et al., "Membrane penetration of liposome by novel peptide fusion protein", The Molecular Biology Society of Japan, The 41st annual conference of the Molecular Biology Society of Japan, 2018, 3P-0745, entire text, non-official translation.

*Primary Examiner* — Sergio Coffa
(74) *Attorney, Agent, or Firm* — Locke Lord LLP

(57) ABSTRACT

The purpose of the present invention is to provide a method for producing a peptide that interacts with a lipid bilayer, and a lipid-bilayer-penetrating peptide obtained through the method. Provided is a lipid-bilayer-penetrating peptide constructed from 10 to 100 amino acids, the peptide having an amino acid sequence that penetrates the lipid bilayer at the C-terminal, and having an amino acid sequence with at least six contiguous arginine at the N-terminal. Also provided is a construct for producing a lipid-bilayer-penetrating peptide, the construct including, from the 5' end toward the 3' end, a tag region 1, a region 1 for incorporating a fluorescent protein gene sequence, a fluorescent protein gene region, a region 2 for incorporating a fluorescent protein gene sequence, a random region, and a stop codon region, and the construct being such that the random region has the aforementioned sequences.

9 Claims, 21 Drawing Sheets
Specification includes a Sequence Listing.

Construct for a peptide binding with N-terminal (LBP1) production

Fig. 2A

LTRKRRRRRRTKTRPDARPIVRSPLSKSHR (SEQ ID NO: 8)
└┘ └─────┘ └──┘ └──────────┘ └────┘
Er    Dr      Cr      Br         Ar
              LBPr1

Fig. 2B

RHSKSRRRRRRKRRTKTLPSRVIPRADPTL (SEQ ID NO: 9)
└───┘ └─────┘ └──┘ └──────────┘ └┘
  A      D      C       B       E
              LBPr2

Fig. 2C

TLRRRRRRKRRTKTLPSRVIPRADPRHSKS (SEQ ID NO: 10)
└┘ └─────┘ └──┘ └──────────┘ └───┘
E     D     C        B         A
              LBPr3

Fig. 2D

(SEQ ID NO: 13)
Schematic figure of the construct for the peptide binding
with C-terminal (LBPr1) production

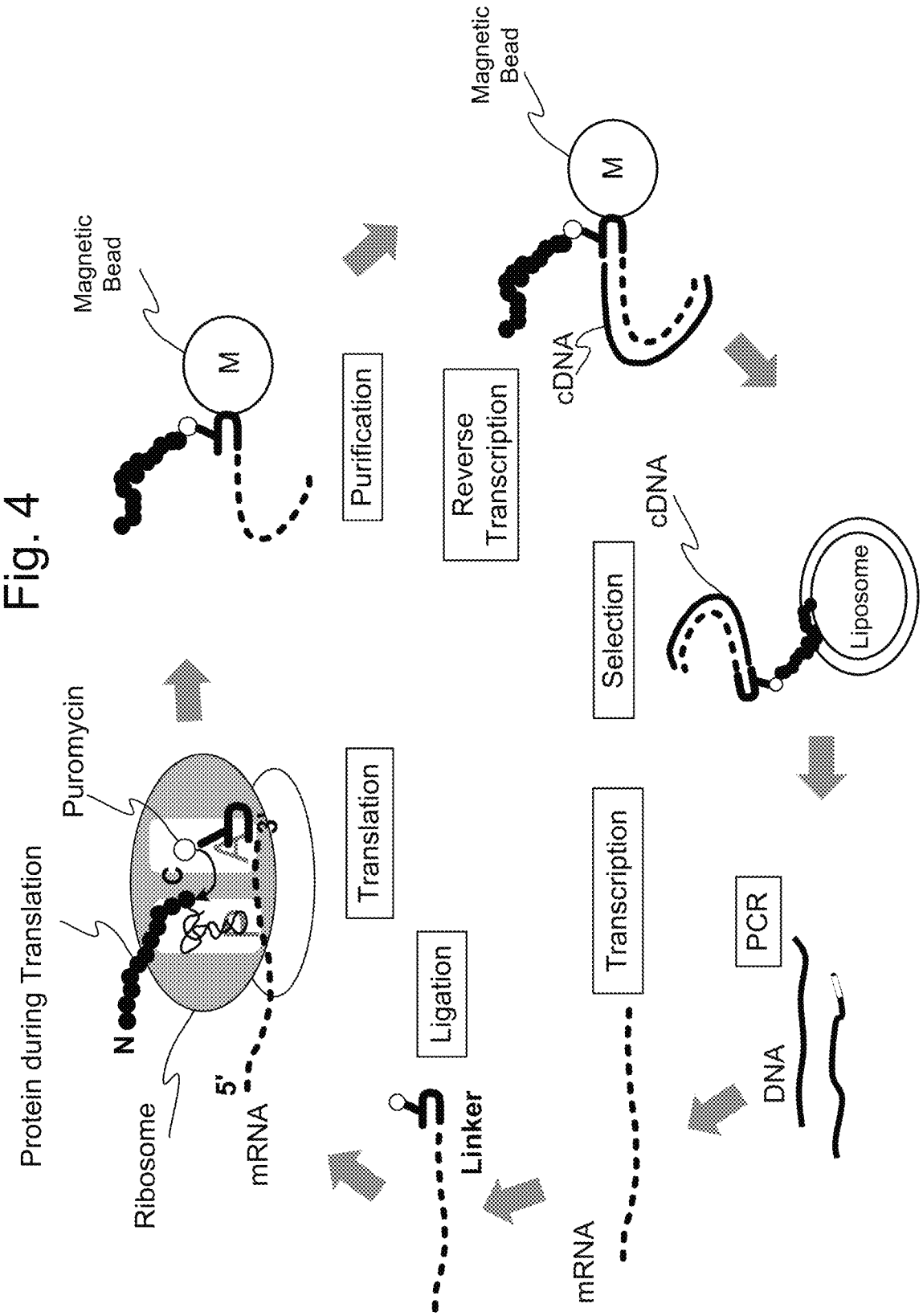

Fig. 5A    Insert Sequence    
Fig. 5B  Template (pET21α vector comprising the present sequence)
(SEQ ID NO: 13)
Fig. 5C PCR Product
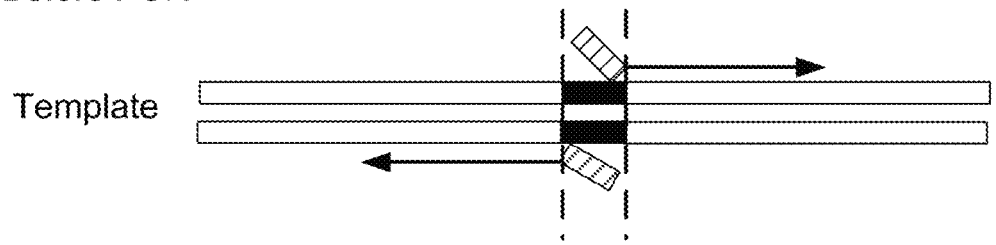
(SEQ ID NO: 13)
Fig. 5D  Before PCR
Template
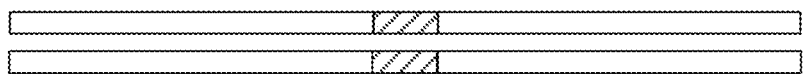
After PCR

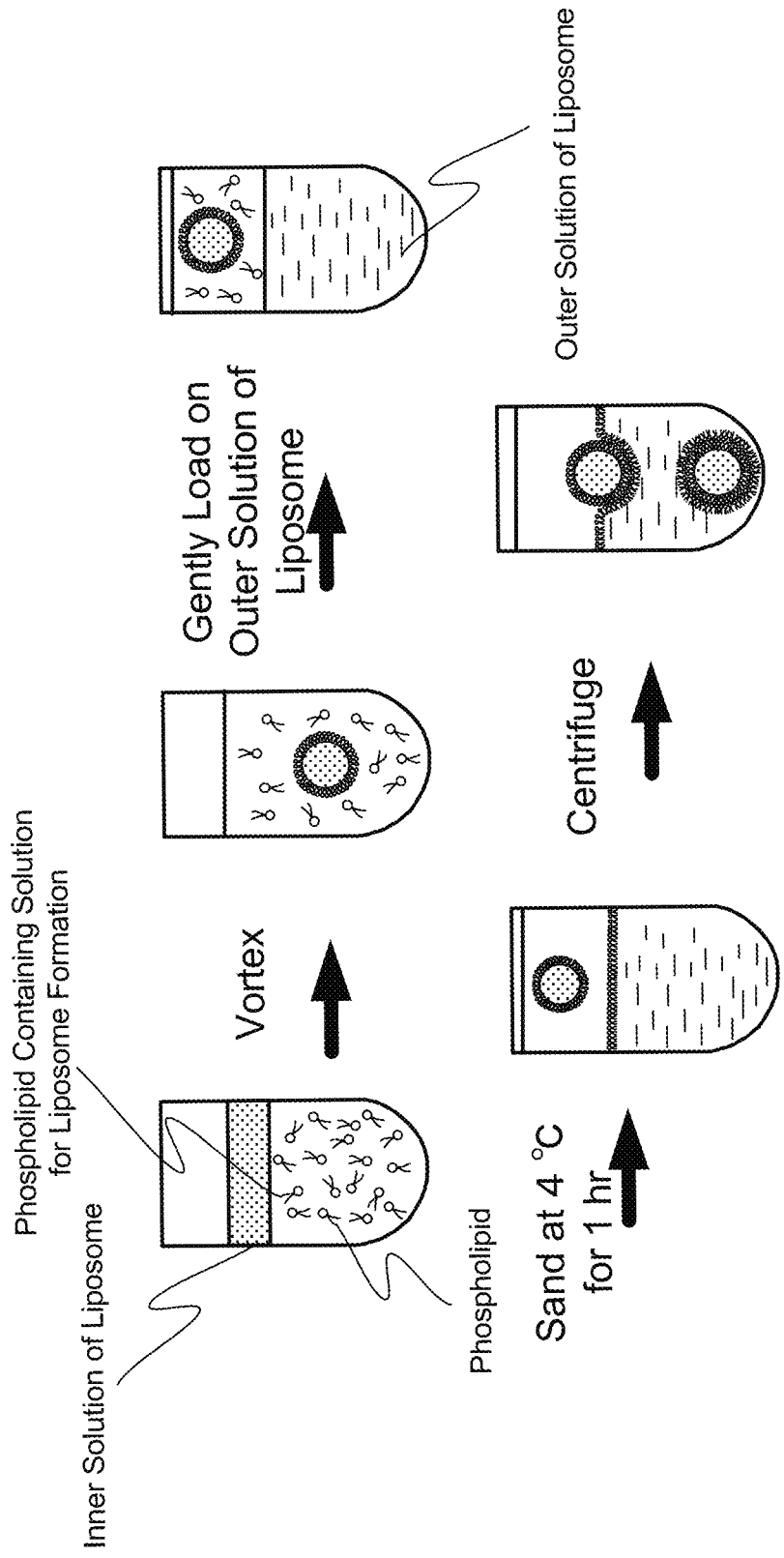

M-Cherry-LBPr1 is solely incorporated in DOPC liposome

Fig. 8A  Inner Solution of Liposome: 1 µM mCherry
Outer Solution of Liposome: : 1 µM GFP
Fig. 8B
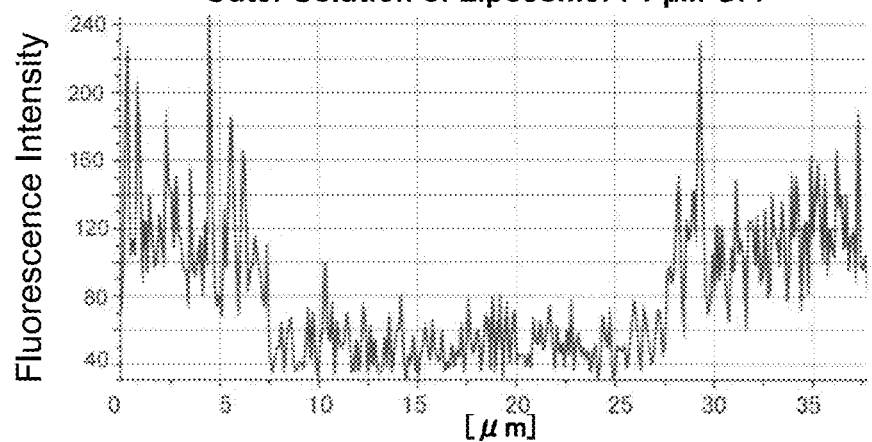
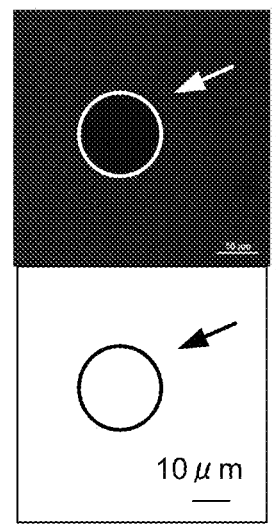
Fig. 8C  Inner Solution of Liposome: 1 µM GFP-LBPr1 Fusion Protein
Outer Solution of Liposome: : 1 µM GFP
Fig. 8D
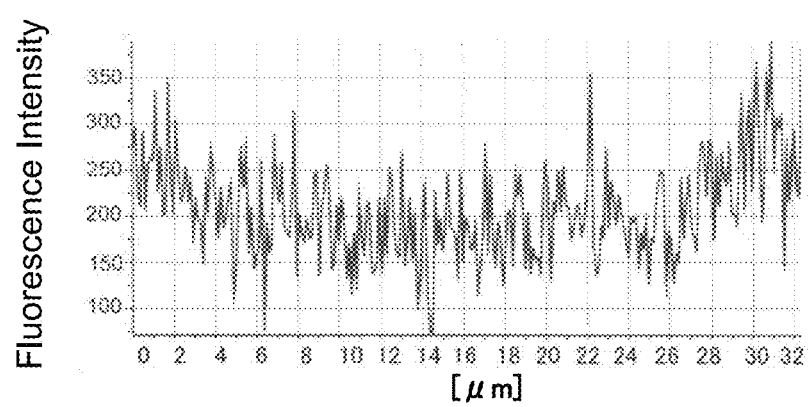
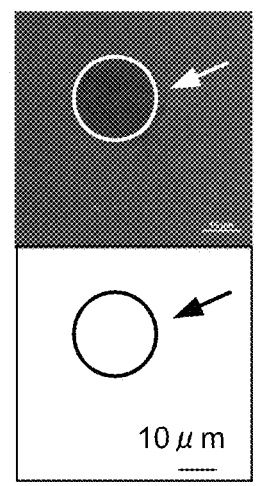

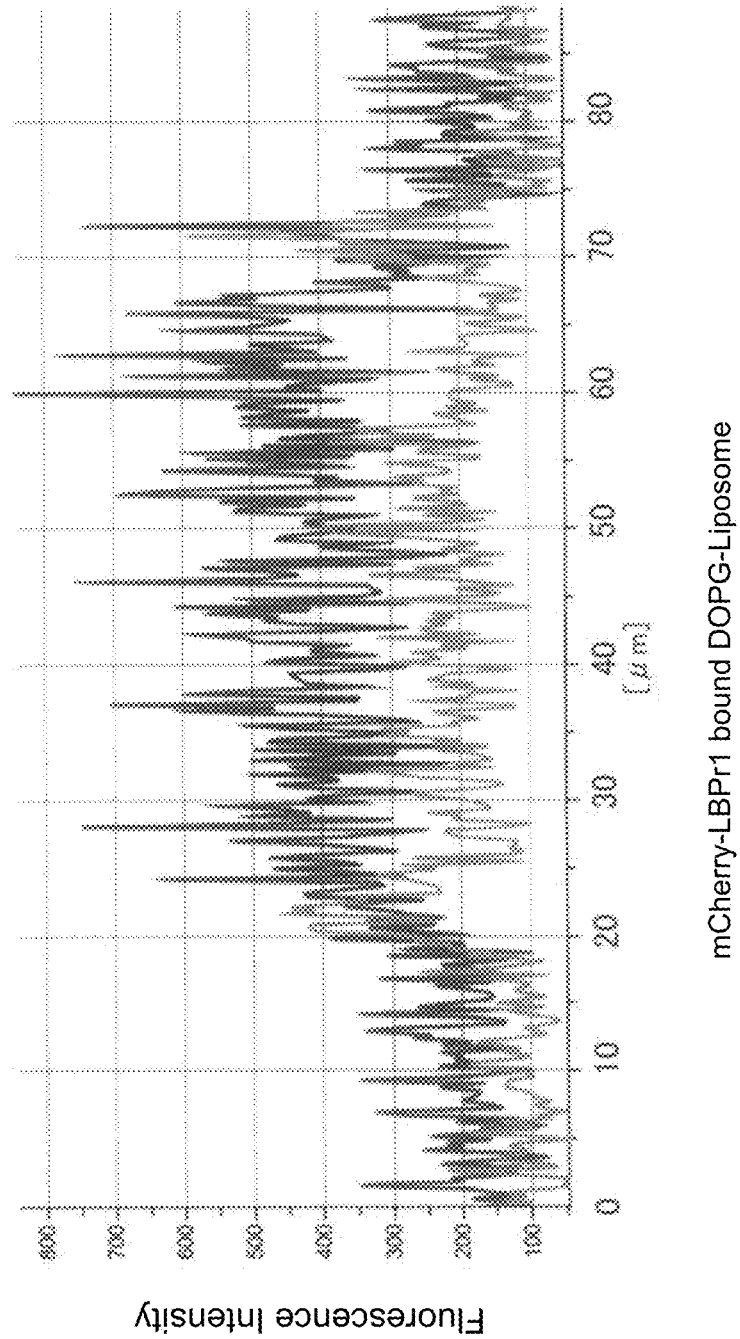

Fig. 14 (con't)
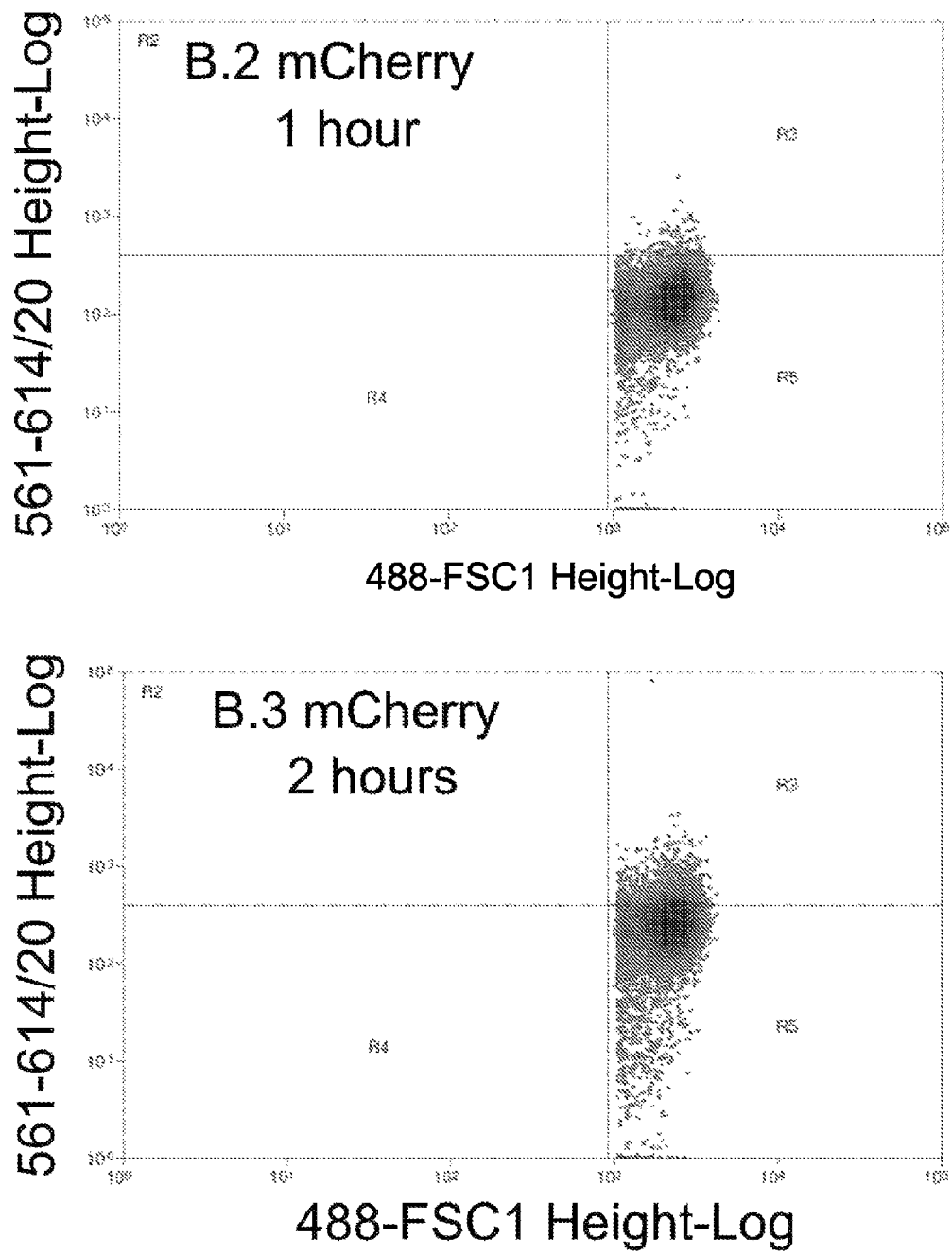

Fig. 14 (con't)
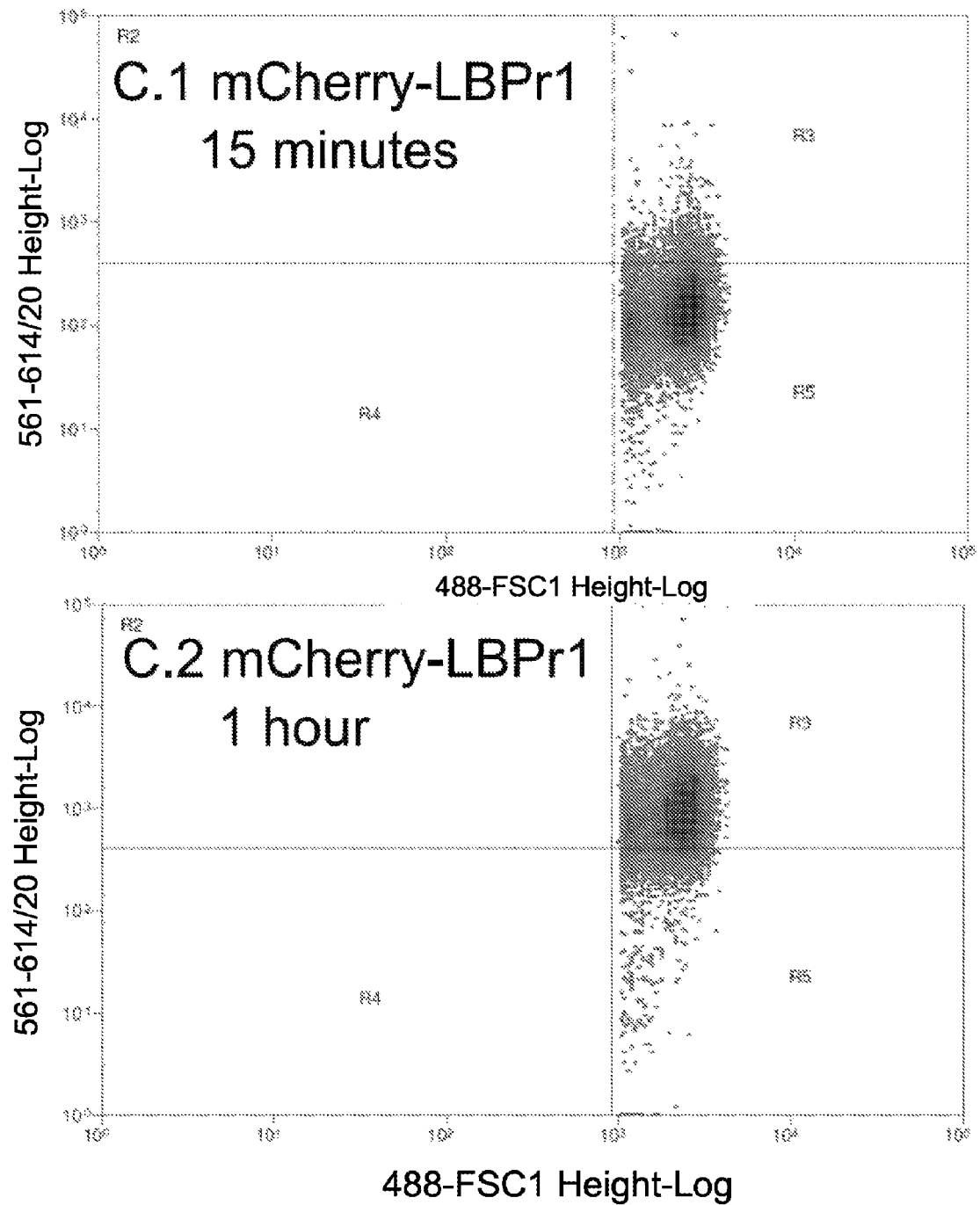

Fig. 14 (con't)
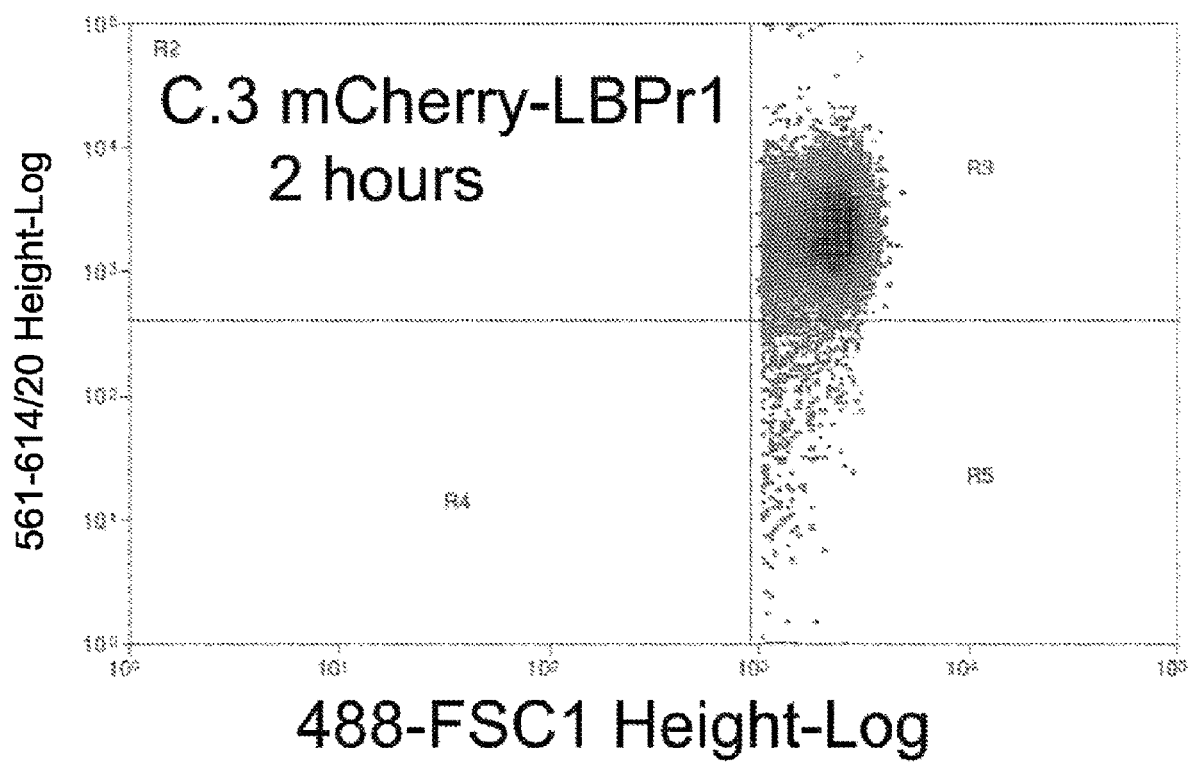

Confocal microscope observation, after incubation of HeLa cells with mCherry–LBPr1 or mCherry at 37 °C for 5% $CO_2$ incubator for 2 hours (DMEM(−)), and then washed.

Fig. 17
Fig. 17A
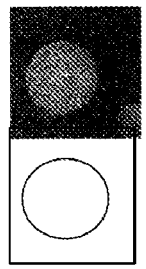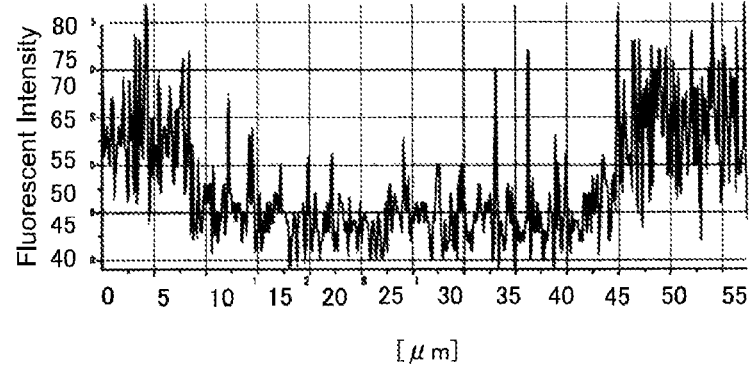
Fig. 17B
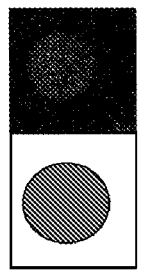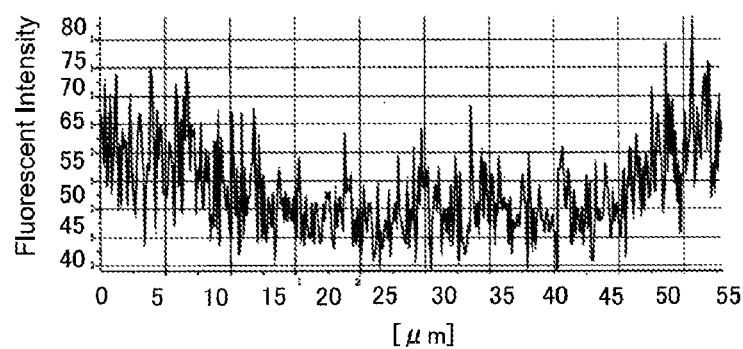
Fig. 17C
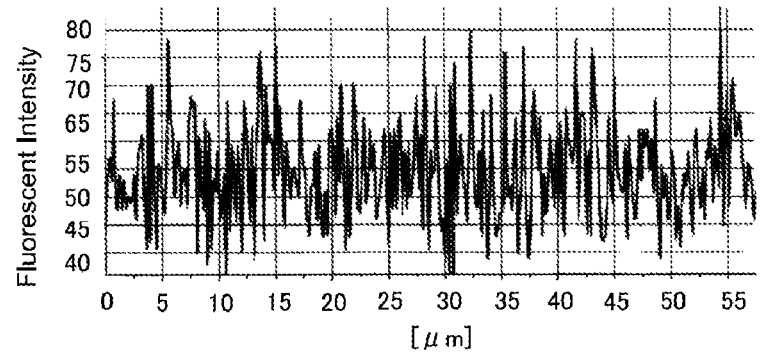

Fluorescence Intensity ration, when mCherry-LBPr1 Fusion
Protein or mCherry in mCherry-R8 Fusion Protein (n=10)

US 12,152,086 B2

```
SEQUENCE LISTING

<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: Block A, which is asfragment of a peptide
      incteract with Liposorm
<220> FEATURE:
<221> NAME/KEY: PEPTIDE
<222> LOCATION: (1)..(10)

<400> SEQUENCE: 1

Pro Asp Ala Arg Pro Ile Val Arg Ser Pro Leu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Block B, which is a fragment of liposome
      interaction peptide
<220> FEATURE:
<221> NAME/KEY: PEPTIDE
<222> LOCATION: (1)..(10)

<400> SEQUENCE: 2

Leu Pro Ser Arg Val Ile Pro Arg Ala Asp Pro
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Block D, which is a fragment of liposome
      interaction peptide
<220> FEATURE:
<221> NAME/KEY: PEPTIDE
<222> LOCATION: (1)..(8)

<400> SEQUENCE: 3

Arg Xaa Arg Arg Arg Arg Xaa Arg
1               5
```

```
<210> SEQ ID NO 4
<211> LENGTH: 4
<212> TYPE: PRT
<213> ORGANISM: Artificial Sequence
<220> FEATURE:
<223> OTHER INFORMATION: Block Cr, which is a fragment of liposome
      interaction peptide having Ra rverse sequence of Block C
<220> FEATURE:
<221> NAME/KEY: PEPTIDE
<222> LOCATION: (1)..(4)

<400> SEQUENCE: 4

Thr Lys Thr Arg
1

<210> SEQ ID NO 5
<211> LENGTH: 4
<212> TYPE: PRT
<213> ORGANISM: Artificial Sequence
<220> FEATURE:
<223> OTHER INFORMATION: Block C, which is a fragment of liposome
      interaction peptide
<220> FEATURE:
<221> NAME/KEY: PEPTIDE
<222> LOCATION: (1)..(4)

<400> SEQUENCE: 5

Arg Thr Lys Thr
1

<210> SEQ ID NO 6
<211> LENGTH: 5
<212> TYPE: PRT
<213> ORGANISM: Artificial Sequence
<220> FEATURE:
<223> OTHER INFORMATION: Block A, which is a fragment of liposome
      interaction peptide
<220> FEATURE:
<221> NAME/KEY: PEPTIDE
<222> LOCATION: (1)..(5)

<400> SEQUENCE: 6

Arg His Ser Lys Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Block Ar, which is a fragment of liposome
      interaction peptide having a reverse sequence of Block A
<220> FEATURE:
<221> NAME/KEY: PEPTIDE
<222> LOCATION: (1)..(5)

<400> SEQUENCE: 7

Ser Lys Ser His Arg
1               5

<210> SEQ ID NO 8
<211> LENGTH: 30
<212> TYPE: PRT
<213> ORGANISM: Artificial Sequence
<220> FEATURE:
<223> OTHER INFORMATION: Peptide pass through libid double layer by
      using C-terminal
<220> FEATURE:
<221> NAME/KEY: PEPTIDE
<222> LOCATION: (1)..(30)
<223> OTHER INFORMATION: LBPr1
```

```
<400> SEQUENCE: 8

Leu Thr Arg Lys Arg Arg Arg Arg Arg Thr Lys Thr Arg Pro Asp
1               5                   10                  15

Ala Arg Pro Ile Val Arg Ser Pro Leu Ser Lys Ser His Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Peptide binds to a liposome at C-terminal
<220> FEATURE:
<221> NAME/KEY: PEPTIDE
<222> LOCATION: (1)..(30)
<223> OTHER INFORMATION: LBPr2

<400> SEQUENCE: 9

Arg His Ser Lys Ser Arg Arg Arg Arg Lys Arg Arg Thr Lys
1               5                   10                  15

Thr Leu Pro Ser Arg Val Ile Pro Arg Ala Asp Pro Thr Leu
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Peptide binds to a liposome C-terminal
<220> FEATURE:
<221> NAME/KEY: PEPTIDE
<222> LOCATION: (1)..(30)
<223> OTHER INFORMATION: LBPr3

<400> SEQUENCE: 10

Thr Leu Arg Arg Arg Arg Arg Arg Lys Arg Arg Thr Lys Thr Leu Pro
1               5                   10                  15

Ser Arg Val Ile Pro Arg Ala Asp Pro Arg His Ser Lys Ser
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Peptide binds to a liposome at N-terminal
<220> FEATURE:
<221> NAME/KEY: PEPTIDE
<222> LOCATION: (1)..(30)
<223> OTHER INFORMATION: LBP1

<400> SEQUENCE: 11

Arg His Ser Lys Ser Leu Pro Ser Arg Val Ile Pro Arg Ala Asp Pro
1               5                   10                  15

Arg Thr Lys Thr Arg Arg Arg Arg Arg Lys Arg Thr Leu
            20                  25                  30

<210> SEQ ID NO 12
<211> LENGTH: 43
<212> TYPE: DNA
<213> ORGANISM: Artificial Sequence
<220> FEATURE:
<223> OTHER INFORMATION: Linker for obtainig the peptide defined as
      Seruqnce Nos. 8 to 10
<220> FEATURE:
<221> NAME/KEY: misc_binding
```

```
<222> LOCATION: (1)..(43)
<223> OTHER INFORMATION: Backbone of cnvK linker, Y shows AminoC6-dT, N
      shows cyanovinyl carbasol
<220> FEATURE:
<221> NAME/KEY: misc_binding
<222> LOCATION: (1)..(43)
<223> OTHER INFORMATION: Backbone of cnvK linker, N shows riboG, K shows
      cyanovinyl carbasol
<220> FEATURE:
<221> NAME/KEY: misc_feature
<222> LOCATION: (21)..(21)
<223> OTHER INFORMATION: n is a, c, g, or t

<400> SEQUENCE: 12
aaaaaaaaaa aaaaaaaaaa ntttccakgc cgcccccgt cct                    43
```

LIPOSOME BINDING PEPTIDE, CONSTRUCT FOR MANUFACTURING THE LIPOSOME BINDING PEPTIDE, AND LIPOSOME

TECHNICAL FIELD

The present invention relates to a liposome binding peptide, a construct for manufacturing thereof and a liposome.

BACKGROUND OF THE INVENTION

A liposome composed of a lipid bilayer has been found in 1960s. Since its finding, it is attracting widespread attention. Such a conventionally known liposome is defined as a vesicle having an amphiphilic membrane being composed of the lipid bilayer. The liposome comprises phospholipids, one of biological components, and it has properties an excellent biocompatibility, low toxicity or antigenicity, and it is conveniently prepared, and it may encapsulate a variety of fat-soluble or water-soluble drugs.

When the liposome having a simple composition, which is composed of the phospholipid only, is administrated i.v., it is captured by reticuloendothelial system, abbreviated as RES, that is involved in a biological defense through phagocytosis of a foreign body, and rapidly eliminated. Namely, the liposome has the problems of less stability or retention in blood so that it cases the leakage of the encapsulated drug into the blood. Therefore, it is tried that the surface of the liposome is modified by polyethylene glycol, abbreviated as PEG, peptides, or specific proteins such as antibodies, Protein A, and the like; thereby retaining them longer in blood to use it as a carrier for drug delivery (See, the non-patent document 1, hereinbelow, it is referred to as the prior art 1).

Also, as a modified technique without use of particular phospholipid, it is known to use a liposome binding peptide being composed of 30 amino acids that binds to the liposome with N-terminal (See the non-patent document 1, hereinbelow, it is referred to as the prior art 2).

On the other hand, recently, there is the problem of appearance for antibiotics resistant strains, and antibacterial peptides, abbreviated as AMP, is focused as a replacement of the antibiotics. The antibacterial peptide is the generic term of the peptide showing antibacterial effects by forming a pore in the cell membrane. Concretely, there are mentioned the peptide such as Magainin 2, Buforin 2, and the like (see, the non-patent document 2, hereinbelow, it is referred to as the prior art 3).

Also, it is known the peptide which is referred to as cell-penetrating peptide, CPPs. CPP is the peptide that enables to incorporate a membrane impermeable substance, for example, the peptide or protein such as the antibody and the like, into the cell. Concretely, TAT-peptide, or octa-arginine, hereinbelow, they are referred to as "R8 peptide", "octa-arginine", or "R8" are known (see, the nonpatent document 3).

In general, the drug is administered to the body and then it is metabolized to exhibit the effects. However, it is known that the drug delivered to the tissues other than the target tissues or organs, hereinbelow, they are collectively referred to as the "target tissues and the like", is excreted as an unchanged drug without providing any pharmaceutical effects, or causes serious side effects. Therefore, in order to deliver the drug to the target tissues and the like, drug delivery techniques for controlling pharmacokinetics thereof temporally or spatially are developed. These techniques are referred to as Drug Delivery System, DDS.

PRIOR ART

Non-Patent Documents

[Non-patent document 1] Kobayashi, S et al., (2017) Chem. Commun., 2017, 53, 3458-3461

[Non-patent document 2] Maria S. Zharkova et al., "Application of Antimicrobial Peptides of the Innate Immune System in Combination With Conventional Antibiotics-A Novel Way to Combat Antibiotic Resistance?" Frontiers in Cellular and Infection Microbiology, Volume 9, Article 128, April 2019, pp. 1-23.

[Non-patent document 3] Amr Selim Abu Lila et al., "Liposomal Delivery Systems: Design Optimization and Current Applications," The Pharmaceutical Society of Japan, Biol. Pharm. Bull., Vol. 40, No. 1, 2017, pp. 1-10.

SUMMARY OF THE INVENTION

Problems to be Solved by the Invention

The prior art 1 is an excellent invention from the view point that it improves the stability or retentivity of the liposome in blood. However, as is commonly known, since the liposome does not have targeting property, it has the problem that it cannot deliver encapsulated drug to the target tissues and the like.

Also, the prior art 2 is the excellent invention that it is capable of modifying the liposome without the use of specific phospholipids. However, since LBP binds to the liposome at its N-terminal of the peptide, there is the problem that C-terminal of the peptide, which is difficult to be modified, is existed on a surface of the liposome. The prior art 3 has the problem that the antibacterial peptide makes pores in the cell membrane, thereby content in the liposome leaks out.

Namely, there are strong needs for the liposome having high stability or high retentivity in blood, and having high targeting property with the modified surface, of which surface is modified without leak out of the content encapsulated in the liposome.

Furthermore, there is another strong need for the technique to prepare a variety of the liposomes depending on the applications is manufactured conveniently.

Means for Solving the Problem

In order to respond the above demands, the present inventors proceeded with diligent research under the above-mentioned circumstances, and completed present invention.

Namely, the object of the present invention is to provide a peptide interacting with a membrane formed by a lipid bilayer. Also, another object of the present invention is to provide a construct for manufacturing the peptide interacting with the lipid bilayer. Furthermore, another object of the present invention is to provide a liposome bound to the peptide.

An aspect of the present invention is a peptide interacting with a lipid bilayer, comprising a binding region for binding said lipid bilayer at C-terminal side thereof, and a basic region being composed of at least 6 basic amino acids at N-terminal side, wherein said peptide is composed of 10 to 100 amino acids. Here, it is preferable that the binding region is composed of a certain number of amino acids, and more than half thereof is hydrophobic amino acids. Also, it is preferable that the binding region comprises either of an amino acid sequence represented in SEQ ID NO. 1 or 2 in the sequence listing (see, Table 1 in below).

The basic region preferably comprises said amino acid sequence represented in SEQ ID NO. 3 (see, Table 1 in below). Two X in SEQ ID NO. 3 represent arginine or lysine, however both of X do not simultaneously become arginine or lysine. Here, the peptide is preferably composed of 25 to 40 amino acids.

The peptide of the present invention preferably comprises: (a) either of said amino acid sequence represented in SEQ ID NO. 4 or 5 between said biding region and said basic region (see, Table 1 in below): (b) any one of the amino acid sequence composing N-terminal thereof, selected from the group consisting of LT, TL, and the amino acid sequence represented in SEQ ID NO. 6 in the sequence listing (see, Table 1 in below); and (c) any one of the amino acid sequence composing C-terminal thereof, selected from the group consisting of TL, and the amino acid sequences shown in SEQ ID NO. 7 and SEQ ID NO. 8 in the sequence listing (see, Table 1 in below).

TABLE 1

| Name of Blocks*[1] | Amino Acid Sequence | SEQ ID NO. |
|---|---|---|
| Br*[2] | PDARPIVRSPL | 1 |
| B | LPSRVIPRADP | 2 |
| D | RXRRRRXR | 3 |
| Cr* | TKTR | 4 |
| C | RTKT | 5 |
| A | RHSKS | 6 |
| Ar* | SKSHR | 7 |
| ErDrCrBrAr | LTRKRRRRRRTKTRPDARPIVRSPLSKSHR | 8 |
| ADCBD | RHSKSRRRRRRKRRTKTLPSRVIPRADPTL | 9 |
| EDCBA | TLRRRRRRKRRTKTLPSRVIPRADPRHSKS | 10 |

*[1]The name of each block is described in below.
*[2]In the table, "r" means that the amino acid sequence of each Block is reverse compared to that without it.

Another aspect of the present invention is the peptide comprising the amino acid sequence of SEQ ID NO. 8, and penetrating a lipid bilayer of the liposome or a cell membrane. Alternatively, it is the peptide comprising the amino acid sequence of SEQ ID NO. 9 or 10, and binding with C-terminal thereof to the lipid bilayer of the liposome or the cell membrane.

Yet another aspect of the present invention is a construct for a fusion protein expression comprising in the direction from 5' end to 3' end: a tag region, a region for incorporating a fluorescent protein gene, a random region and a stop codon. Here, the random reign is the region for incorporating the peptide-coding gene of the present invention. And, the fluorescent protein gene region and the random region are preferably mutually bind through a ligation region (for example, it encodes the amino acid sequence represented in SEQ ID NO. 4 or 5.

The fluorescent protein gene region is ligated to the region for the gene at 5' end. Also, the random reign is directly ligated to stop codon at 3' end. The present invention is the construct for expressing the fusion protein comprising the region 2 incorporating the fluorescent protein gene sequence, the random region, the binding region for binding to the lipid bilayer at C-terminal, and the hydrophobic region being composed of at least 6 hydrophobic amino acids at N-terminal. The construct contains the gene for expressing the fusion protein being composed of 10 to 100 amino acids, and interacts with the lipid bilayer.

Here, the binding region contained in the random region is composed of a certain number of the amino acids, and more than half number of them are hydrophobic. Also, the binding region preferably has an amino acid sequence represented in SEQ ID NO. 1 or SEQ ID NO. 2.

The hydrophobic region included in the random region preferably has an amino acid sequence represented in SEQ ID NO:3, wherein, X is preferably arginine or lysine. Also, the random region preferably is located between the hydrophobic region and the binding region, and comprises the amino acid sequence represented in SEQ IF NO. 4 or SEQ ID NO. 5; it has N-terminal sequence selected from the group consisting of LT, TL, and the amino acid sequence represented in SEQ ID NO. 6, and C-terminal sequence being composed of the amino acid sequence selected from the group consisting of TL, the amino acid sequence represented in SEQ ID NO. 7 and SEQ ID NO. 8. Also, the random region preferably has the any one of the amino acid sequences selected from the group consisting of that represented in SEQ ID NO. 9 to SEQ ID NO. 11.

Yet another aspect of the present invention is a liposome encapsulating the peptide mutually interacting to the lipid bilayer, or the liposome on which the peptide mutually interacting to the lipid bilayer.

Advantageous Effect of the Invention

According to the present invention, the peptide interacts with the lipid bilayer of the liposome or the cell membrane, hereinbelow, it is referred to as "membrane interacting peptide, is provided. Also, according to the present invention, as the membrane interacting peptide, the peptide binds to the lipid bilayer at C-terminal, or penetrates thereof is provided. Further according to the present invention, the construct for expressing the fusion protein comprising the membrane interacting peptide is provided. Furthermore, according to the present invention, the liposome encapsulating the membrane interacting peptide or that on which the peptides bound is provided.

BRIEF EXPLANATION OF DRAWINGS

The patent or application file contains at least one drawing executed in color. Copies of this patent or patent application publication with color drawing(s) will be provided by the Office upon request and payment of the necessary fee.

FIG. 1(A) shows the amino acid sequence of the peptide of the present invention and a schematic figure of divided amino acid sequence into blocks. FIG. 1(B) is a schematic figure showing an expression construct for the fusion protein of LPB1 and mCherry, a fluorescent protein, wherein the peptides described above are randomly incorporated. FIG. 1(C) shows a fluorescent image after the fusion protein and the liposome are incubated in upper column and the diagram thereof in lower column. FIG. 1(D) is a confocal laser micro spectroscopic image in the upper column and the diagram thereof in the lower column.

FIG. 2(A) to (D) shows the membrane interacting peptide of the present invention. FIGS. 2 (A) to (C) show the amino acid sequence of the membrane interacting peptide, and the arrangement of the blocks shown in FIG. 1. FIG. 2(D) is the schematic figure showing the construct for the fusion protein expression of the membrane interacting peptide of the present invention and the fluorescent protein, mCherry, wherein the peptides shown in FIGS. 2(A) to (C) are incorporated in the random region.

FIG. 4 is the schematic figure showing the screening method for the membrane interacting peptide of the present invention.

FIG. 5(A) to (D) is the schematic figure showing an example of the method for replacing the random region in the membrane interacting peptide of the present invention with another peptide.

FIG. 6 is the schematic figure showing the preparation method of the liposome which incorporates the inner solution of the liposome different from the outer solution thereof.

FIG. 8(A) to (D) shows the study results for the incorporation of GFP-LBPr1 after the incubation of it and the liposome.

FIG. 10 shows the observation results of the change when the liposome (DOPG) and mCherry-LBPr1 are incubated by using the confocal laser scanning microscope (Olympus Corporation).

FIG. 17(A) to (C) shows the comparison result of the membrane penetration capability of mCherry, mCherry-LBPr1, and mCherry-R8.

MODE OF CARRYING OUT THE INVENTION

Hereinbelow, the present invention is explained in detail, referring to the embodiment of the present invention.

One embodiment of the present invention is a peptide interacting with a lipid bilayer at C-terminal, comprising (A1) a binding region for binding said lipid bilayer at C terminal side thereof, (A2) a basic region being composed of at least 6 basic amino acids at N terminal side, (A3) and a region composed of hydrophobic rich amino acids ligated to 3' side of said basic region through a sequence composed of 4 amino acids, and (A4) said peptide is composed of 10 to 100 amino acids. Here, it is preferable that the binding region comprises a certain number of the amino acids, and more than half of them are the hydrophobic amino acids; because the peptide of the present invention interacts to the liposome with its C-terminal. Also, it is preferable that the basic region has the structure being composed of not less than 6 arginine, because of conducting the stable interaction between the peptide and the liposome.

In the present specification, the terms, "interaction with the lipid bilayer" contains followings: that the peptide binds to the lipid bilayer at its C-terminal; that it binds to the lipid bilayer at its C-terminal and then it penetrates the membrane of the liposome formed by the lipid bilayer; that it is incorporated into the space in the membrane formed by the lipid bilayer, namely, the liposome, by penetration through the membrane; and that it is incorporated into inside of the cell.

Also, it is preferable that the amino acid numbers composing the present peptide is, for example, from 25 to 40, from view points of the stability of the interaction between the liposome, and operability thereof. In below, the present invention is explained, illustrating when it is composed of 30 amino acids as the example.

Figure 1A:
FIG. 1(A) to (D) shows the peptide, which is invented by the inventors of the present invention, binds to the lipid bilayer at N terminal thereof.

As shown in FIG. 1(A), the membrane interacting peptide of the present invention has the sequence designed based on the amino acid sequence of the liposome binding protein at N-terminal (LBP1). Here, the term, "the sequence designed based on the amino acid sequence", is defined that the sequence wherein the amino acid sequence of LBP1 is divided into 5 blocks based on functions thereof to change the order of the blocks, or that contains the blocks prepared by rearranging the order of the amino acids thereof (see, FIG. 2 (A) to (C)).

As shown in FIG. 1 (A), the amino acid sequence of LBP1 is divided into 5 blocks based on their functions: Block A being composed of 5 amino acids located at N-terminal; next Block B being composed of 11 amino acids rich in hydrophobicity; Block C being composed of 4 amino acids; next Block D being composed of 8 amino acids rich in basic amino acids; and Block E being composed of 2 amino acids.

Here, Block B is composed of at least more than half numbers of the amino acids thereof are hydrophobic, and it is arranged close to N-terminal of the peptide. Note that the amino acid sequence composing Block B may be reverse sequence of Block B (See, table 1).

Block D contains 6 or more sequentially continuing arginine, which is the basic amino acid, and arranged close to N-terminal of the peptide. The sequence of Block D is shown in Table 1, and two X contained in SEQ ID NO. 3 are not simultaneously become arginine or lysine, and if one is arginine, another is lysine.

As shown in FIGS. 2 (A) to (C), the order of Blocks A, C, and E is arranged from N-terminal to C-terminal: at first, Block E or Block A; at last Block A or Block E; and other 3 Blocks are between them. Namely, these 3 blocks located between at N-terminal and C-terminal, they are arranged in the order of Block D, C and B. Here, the amino acid sequence in each block may be in the reverse order as described above.

The peptide having such amino acid sequence may be used to manufacture the construct by synthesizing DNA coding thereof, being incorporated into a vector which contains predetermined gene sequences, and then used to express thereof. The DNA synthesis may be conducted according to the conventional method, or ordered to manufacturer, companies who accept DNA synthesis, for example, such as GeneWorld Inc.

Another embodiment of the present invention is the construct for protein expression comprising DNA coding the amino acid sequence. The expression construct of the present invention comprises a tag region, a fluorescent protein gene region, a random region for integrating the gene coding the peptide of the present invention, and the stop codon sequentially in the direction from 5' end to 3' end. The fluorescent protein gene region and the random region are ligated via ligating region. Then, it has a region for integrating the fluorescent protein gene at 5' end, and the random region is directly ligated to the stop codon (See, FIG. 2(D)).

Figure 1B:
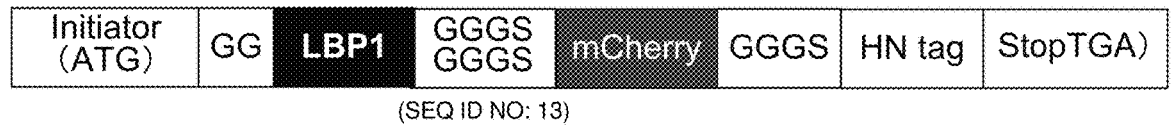

The structure of the expression construct of the present invention is largely different from the construct for LBP1 expression in many aspects, LBP1 ligates to the liposome at N-terminal thereof (see, FIG. 1(B)). Concretely, there are differences such that: it does not comprise an initiator, ATG; the order of the random region to which LBP is integrated and the fluorescent gene region; the integrated position of the flag gene is different.

Here, as a tag to be used as a tag region, for example, FLAG (registered trademark, DYKDDDDK (SEQ ID NO: 14), DDDDK (SEQ ID NO: 15), and the like are known), HA, His, Myc, V5, HN, and the like are commercially available, and they may be used. However, it is preferable to use tags such as HA, His and HN and the like, from the view point of the treatment after the purification of the expression protein. Also, in the fluorescent protein gene region, proteins emitting a variety of fluorescence such as red fluorescence, green fluorescence, and the like, may be incorporated. Such fluorescent proteins are commercially available, and mCherry, AcGFP1, DsRed-monomer are favorably used from the view point of fluorescence intensity. As the region for integrating the fluorescent protein gene, there are mentioned, for example, the long and highly flexible linker sequence such as GGGS and the like, which is referred to as a "ligation sequence" herein below, and as the ligation sequence, there are mentioned such as GGGSGGGS (SEQ ID NO: 13), and the like.

Also, DNA sequence encoding the membrane interacting peptide of the present invention is integrated into the random region to manufacture the construct. By using the construct, a fusion protein of the present peptide and a fluorescent protein may be expressed. After that, the expressed protein is incubated with the liposome prepared by using desired phospholipid, thereby the interaction between the present peptide and the liposome may be studied.

Here, as the membrane interacting peptide of the present invention, there are mentioned, for example, such as the peptide being composed of from 10 to 100 amino acid, having the binding region at the C-terminal thereof, and the hydrophobic region comprising at least 6 hydrophobic amino acids at N-terminal thereof. Among them, the peptide shown in SEQ ID NO. 8 to 10, hereinbelow, they are referred to as "LBPr1", "LBPr2", and "LBPr3" are preferable, because they conduct unique interaction with the phospholipid forming the liposome membrane at C-terminal thereof.

Above-mentioned LBP1 is the peptide binding to the liposome at its N-terminal. When it is interacted with the liposome, the phospholipid bilayer emits red fluorescence so that the fluorescent image shown in FIG. 1 (C) in the upper column is obtained. When the confocal laser scanning microscope is used, the image shown in FIG. 1 (D) in the upper column is obtained. Lower columns of FIGS. 1 (C) and 1 (D) are diagrams obtained by tracing the images of their upper columns.

As described above, the peptide used as the random region of the construct of the present invention is prepared by using Block A to E, which are obtained by dividing amino acid sequence of LBP1 into 5 blocks, and rearranged in a variety of orders; after that it is subjected to cDNA display method described later to conduct desired rounds to select.

The random region is designed as the region for expressing the membrane interacting peptide of the present invention in a desirable length. It is preferable composed of the amino acids number from 10 to 100, because its operativity for being incorporated into the fusion protein expression construct. It is preferable that the region is composed from 25 to 40 amino acid residues, because it has good operativity described above and is makes the selection easier by using cDNA display method.

Another embodiment of the present invention is the liposome which encapsulated the membrane interacting peptide described above or presenting thereof on the its surface.

Thickness of the liposome membrane is defined by the carbon numbers of the fatty acid forming the liposome. Therefore, it is preferable for the amino acid residue number being increased or decreased appropriately, depending on the thickness of the phospholipid forming the liposome (see, FIG. 3). When the peptide length matches the thickness of the lipid bilayer, the peptide interacts with the liposome so as to stick into the membrane, which makes the interaction more stable.

The amino acid composition of the membrane interacting peptide is preferably 50 to 70% of polar basic amino acids, 15 to 29% of polar non-charged amino acid, 10 to 20% of the hydrophobic amino acids, and 1 to 5% of polar acidic amino acids, when the total amino acid number composing the peptide is set to 100; because it enables to obtain a variety of the peptides interacting with the liposome by using cDNA display method described below. The random region is preferably composed of 30 to 40 amino acid residues, and its amino acid composition is composed of 60% of the polar basic amino acids, 23.2% of the polar non-charged amino acid, 15% of the hydrophobic amino acids, and 1.8% of the polar acidic amino acids, because the peptide has the properties such that it penetrates through the liposome membrane to be encapsulated in the liposome.

Also, the polar non-charged amino acids are glycine, serine, threonine, asparagine (Asn) and glutamine (Gln). It is preferable that the content amounts of glycine, serine and threonine are not less than 15%, and both glycine and serine are contained in the equal amount; because it enables to obtain the peptide having higher liposome binding activity by using in vitro screening described later.

Also, it is preferable that the hydrophobic peptides are alanine, valine, leucine, isoleucine, methionine, and proline, and both proline and leucine are contained in the equal amount; because it enables to obtain the peptide having higher liposome binding activity by using in vitro screening described later.

Raw materials for the liposome of the present invention are not particularly limited, however, for example, 1,2-Dioleoyl-sn-glycero-3-phosphoglycerol, which is referred to as "DOPG", hereinbelow, and/or 1,2-Dioleoyl-sn-glycero-3-phosphocholine, which is referred to as "DOPC" may be employed (see, FIG. 3). Here, the liposome may be constituted by using single phospholipid, either DOPG or DOPC, which is referred to as a "simple liposome" herein blow, or by using both of DOPG and DOPC, which is referred to as a "mixed liposome" hereinbelow.

By coexisting either of the simple liposome or the mixed liposome and the fusion protein of the present invention, the reactivities of the constituent material of the liposome and the membrane interacting peptide are studied.

For example, when the simple liposome composed of DOPC and LBPr1 are coexisted, it is confirmed whether LBPr1 is only bound to the membrane or it penetrates through the membrane and incorporated into inside thereof by tracing the fluorescence from the fluorescent protein.

Furthermore, the membrane interacting peptide of the present invention is coexisted with the mixed liposome, it is confirmed whether the interaction between the liposome membrane and the present peptide is changed, depending on the mixed ratio of DOPC and DOPG.

Namely, by changing types of the lipids and the ratio which constitutes the liposome, the change of the interaction between the membrane and the present peptide is studied.

The preparation method of the membrane interacting peptide of the present invention is not particularly limited. For example, it is prepared by using the construct made by the method described above to prepare cDNA library containing cDNA of 106 order; and then the cDNA library is substituted to the cDNA display method for selecting by using in vitro. Here, FIG. 4 shows the screening method of the phospholipid bilayer binding peptide of the present embodiment by using the cDNA display method.

The screening method comprises the steps of: (a1) preparing mRNA; (a2) forming the $1^{st}$ conjugate; (a3) forming the $2^{nd}$ conjugate; (a4) binding to a particle; (a5) forming the 3rd conjugate; (a6) releasing the $3^{rd}$ conjugate; and (a7) selecting.

Firstly, (a1) in mRNA preparation step, mRNA is prepared from the construct by transcription thereof. After that, (a2) in the first conjugate formation step, mRNA obtained in the mRNA preparation step is bound to the linker having puromycin to form the first conjugate. Here, the firstly formed conjugate is linker-mRNA conjugate as described above. Next, (a3) in the second conjugate formation step, a peptide having an amino acid sequence defined by mRNA, which is synthesized by translation from mRNA, and then it is bound to puromycin in the linker. Namely, the second conjugate formed in the step is a peptide-linker-mRNA conjugate.

Next, (a4) in the particle binding step, the second conjugate obtained described above is bound to a magnetic particle. Subsequently, (a5) in the third conjugate formation step, mRNA of the second conjugate bounds to the magnetic particle is reverse transcribed to form cDNA. Therefore, the third conjugate formed here is the peptide-linker-mRNA/cDNA, hereinbelow, it is referred to as "cDNA display". Next, (a6) in the complex releasing step, cDNA display obtained in the third conjugate formation step is released from the magnetic particle, and subsequently, (a7) in the selection step, the released third conjugate is selected by binding to the liposome.

As the cell free translation system, commercially available kits, for example, Retic Lysate IVT Kit (Ambion) and the like may be used. For example, according to a protocol attached to the kit, all of reagents to be used in the cell free translation reaction are gently mixed and then subjected to centrifugation, and then they are placed on an ice. The scale of the reaction solution is about 20 to about 50 µL, and the reagents are mixed in the following order to prepare the reaction solution for the reaction. When the kit is used, about 0.5 to about 1 µL of 20× Translation Mix without Met, about 0.5 to about 1 µL of 20× Translation Mix without Leu, and about 15 to about 20 µL of Retic lysate are carefully mixed by pipetting not from bubbles.

The mixture is added into about 25 to about 50 µL of the sample solution, DEPC water is added to the reaction solution up to of which amount becomes a desirable volume, for example, about 20 to about 30 µL. After that, the solution is again gently mixed not to form the bubbles for conducting the translation reaction at 30° C. for 20 minutes. After the translation reaction, in order to accelerate the ligation between the ligates A and the synthesized protein, about 15 to about 25 µL of KCl solution containing about 2 to about 4M KCl, and 4 to 8 µL of $MgCl_2$ solution containing 0.5 to 2 M of $MgCl_2$ are added to the reaction solution and then reacted at about 37° C. for about 30 to about 50 minutes.

When equivalent amount of about 80 to about 100 pmol of cDNA display molecule are existed in the solution, about 50 to about 70 µL of the magnetic beads, for example, Dynabeads MyOne C1 provided Invitrogen Dynal, is added, and then it is incubated at room temperature for about 15 to about 30 minutes to bind the ligates to shoch the synthesized peptide is presented, the linker-mRNA-peptide ligates, to the surface of the magnetic bead at the linker moiety. Note that the linker with the fluorescent molecule is bound, the localization of the fluorescence on the liposome surface is confirmed.

Next, it is subjected to the reverse transcription of mRNA bound to the ligate by using, for example, ReverTra Ace (TOYOBO), at about 40 to about 44° C. for about 30 minutes to obtain the ligate to which cDNA is bound, the linker-mRNA-peptide-cDNA ligate. Subsequently, the obtained ligate is treated with a suitable enzyme, for example, RNase T1, at about 35 to 38° C. for about 10 minutes to release the ligate to which cDNA is ligated, cDNA display, from the magnetic beads.

As the fluorescent molecule used here, there are mentioned such as fluorescein, GFP and the like.

Next, the preparation method of liposome in the present embodiment.

The preparation method of the liposome comprises the steps of: (b1) preparing the lipid solution; (b2) forming the lipid membrane; (b3) preparing the liposome solution; and (b4) recovering the liposome.

Here, in the lipid solution preparation step (b1), organic solvent containing the lipid is prepared. Also, in the lipid membrane formation step (b2), the lipid solution prepared in the lipid preparation step is dried on the solid phase to form the lipid membrane. In the liposome solution preparation step (b3), Good's buffers are added to the lipid membrane to form liposome solution. In the liposome recovery step (b4), Good's solution containing sugar is added to recover the liposome.

Namely, as the lipid used in the lipid solution preparation step (b1), there are mentioned, for example, DOPG, DOPC and the like. DOPC is preferably used, because it is used for forming giant liposomes being consisting of a single lipid bilayer, which is observed under the optical microscope, and referred to as "vesicle". Also, as the organic solvent, there are mentioned such as dichloromethane, chloroform, carbon tetrachloride, and the like, and chloroform is preferably used, because it makes the operation conveniently.

In order to purify the liposome by using difference of specific gravity of inner solution of the liposome and the outer solution of the solution, Good's buffers containing different sugar at the same concentration are prepared. As solutions containing the sugar for preparing Good's buffers, the following buffers may be prepared: about 10 to about 30 mM of morpholino propane sulfonic acid, hereinbelow, it is referred to as "MOPS", buffer containing about 0.05 to about 0.2M of sucrose, and about 10 to about 30 mM of MOPS buffer containing about 0.05 to about 0.2M of glucose. About 30 to about 50 μL of DOPC (AVT) is dissolved in about 900 to about 1,000 μL of the organic solvent, for example, chloroform, at desirable amount of 0.5 to 2 mM of the lipid solution in chloroform, for example, about 0.75 to about 1.5 mL, is prepared.

A glass petri dish having suitable size, for example, the diameter about 5 cm, is washed by using a detergent and then dried. The entire amount of the chloroform solution is poured into the dish, and spread in the dish entirely. Next, nitrogen gas is introduced into the dish to volatile the organic solvent. Subsequently, a vacuum pump is connected to a desiccator, and the dish is placed therein overnight. For example, about 20 mL of about 20 mM MOPS buffer containing about 0.1 M sucrose is gently poured into the dish not without stirring the lipid membrane. In order to prepare the liposome, the solution is stood at the temperature, about 35 to about 39° C. for about 2 to about 4 hours for its hydration. Hereinbelow, the liposome is sometimes referred to as the "vesicle".

When the liposome is prepared, for example as mentioned above, about 20 mM MOPS buffer, pH about 6.8 to about 7.2, containing about 0.1 M sucrose is used to prepare the liposome incorporated the buffer inside thereof. From the solution containing the liposome, about 1 to about 3 mL portion is taken out, and it is poured into a desired volume of the centrifuge tube, for example, 15 mL, and then the desired amount of MOPS buffer, 20 mM, pH 6.8 to 7.2, containing 0.1 M glucose, for example, about 12 mL is added.

When the specific gravity of the buffer incorporated in the liposome is heavier than that of the outer solution of the liposome, the liposome is floated for the purification. When their specific gravity is revered, the liposome is precipitated by the centrifugation for the purification. When they are precipitated, the liposome accumulated in the bottom of the centrifuge tube is recovered by using a syringe. As described above, the giant unilamellar vesicles which is observed under the optical microscope, which is sometimes referred to as a giant unilamellar vesicles, and herein below, it is referred to as "GUV", is prepared.

Next, in the lipid membrane formation step (b2), the lipid solution obtained in the preparation step is dried on the solid phase to form the lipid membrane. The lipid is dissolved in the organic solvent to be the desirable concentration, for example, in the range of 0.5 to 2 mM, and the solution is spread on the solid phase to form a thin film. As the solid phase used, the glass petri dish is preferable, because the organic solvent is used. After the solution is spread on the solid phase, for example, nitrogen gas is blown to obtain uniform thickness of the thin film. Then, the solid phase on which the thin film is formed is stood overnight, and it is further dried to volatile the organic solvent completely.

Next, in the liposome solution preparation step (b3), Good's buffers, hereinbelow, it is sometimes referred to as a "buffer", containing the sugar of which concentration is desirably adjusted is gently added to the lipid film formed as described above, and then the mixture is stood at the desirable temperature and time to prepare the liposome solution. Here, among Good's buffers, it is preferable to use MOPS, because the buffer is conveniently prepared and stored. It is preferable to use Good's buffers in the concentration range of about 10 to about 50 mM, because of the reaction efficiency.

Also, the sugar added to the buffer, there are mentioned such as sucrose, glucose and the like. The sugar content used is preferable in the range of about 0.05 to about 0.2 mM, because the purification of the liposome, binding of the liposome and the peptide, and the purification of the conjugate of the liposome and the peptide are easily conducted.

For example, about 0.5 to about 2 mM DOPC chloroform solution is prepared, and then it is poured into the glass petri dish. After that, chloroform is removed by blowing nitrogen gas to form thin film of the lipid inside wall of the dish. After that, for example, it is further dried in the desiccator connected to the vacuum pump overnight.

Next, the lipid film is added to about 10 to about 50 mM Good's buffer containing about 0.05 to about 0.2M sugar described above, and incubated in the temperature from 32 to 40° C. for 2 to 5 hours for hydration to form the liposome. For example, the lipid film prepared as described above is added to about 20 mM MOPS buffer containing about 0.05 to 0.2 M sucrose, and then incubated at about 35 to 37° C. for about 2 to 4 hours for hydration. By this, the liposome having the diameter from 0.01 to 10 μm is prepared.

Subsequently, in the liposome recovery step (b4), Good's buffer containing the sugar is added to the liposome solution, and they the mixture is centrifuged to recover the liposome. As the sugar used in the step, there are mentioned such as glucose, sucrose and the like. Glucose is preferably used, because it easily precipitates the liposome.

Good's buffer containing the sugar of the desirable amount is added to the liposome solution prepared as described above and centrifuged to recover the liposome. For example, from 4 to 6 volumes of 10 to 50 mM MOPS containing 0.05 to 2 mM glucose is added to the liposome solution and then centrifuges. By using the solution, the specific gravity of the sucrose containing MOPS incorporated in the liposome becomes heavier than that of the outer solution of the liposome, MOPS containing glucose. Therefore, the liposome is precipitated by simple centrifugation, and the precipitated liposome is recovered by using the syringe and the like.

In order to prevent rejoin of the liposome, the liposome prepared as described above is light shielded and stored at 4° C. until use.

Next, the recovery step of cDNA display interacting to the membrane comprises the steps of: (c1) adding solution; (c2) separating step; and (c3) recovering. In the solution adding step (c1), the solution containing cDNA display is added to the liposome solution containing the liposome obtained as described above. Subsequently, in the separating step (c2), the mixture of the liposome solution and the cDNA display solution is centrifuged, for example, in 5,000×g for 5 minutes at room temperature to separate supernatant. After that, in the recovery step (c3), cDNA display interacting with the liposome is recovered as is. Here, in both case that cDNA display is bound to the liposome, or it is penetrated through the liposome membrane and incorporated in the liposome, they are recovered by using the procedure. As described above, the membrane interacting peptide is obtained.

The construct of the present invention is subjected to inverse PCR, its random region may be replaced to another peptide. For example, as shown in FIGS. 5(A) to 5(D), following are used: as the template, a vector incorporating DNA coding fusion protein of the present peptide and the fluorescent protein, and as primers, for example, desirable primers 1 and 2, to which R8 nucleotide sequence, known as the membrane penetrating peptide, namely Cell Penetrating Peptides abbreviated as CPPs, as the tag.

A DNA strand comprising the random region at the around ½ position from the C-terminal to N-terminal of the vector gene is bound to the primer 1 at the position as shown in FIG. 5(D). Next, the primer 2 is bound to its complementary strand at the same position. Subsequently, PCR is conducted under the desirable conditions, thereby, the fluorescent protein-R8 fusion protein, wherein the present peptide at the random region is replaced to R8 shown in FIG. 5(C).

As described above, by replacing the random position to the peptide comprising the desirable sequence, the properties of the membrane interacting peptide of the present invention are confirmed.

As described above, the present peptide may have the penetrating property to the liposome membrane. When the peptide of the present embodiment has the penetrating property to the liposome membrane, it enables to incorporate a membrane impermeable material into the cell, for example, by fusing it to the substance to be incorporated. Therefore, the peptide may be used as new carrier for drug delivery system, Drug Delivery System, hereinbelow, it is sometimes referred to as "DDS", or a tool for functional analysis application of the intracellular molecules.

The peptide of the present embodiment comprises the amino acid sequence, which binds to the liposome membrane at the C-terminal thereof. This means that it has extremely great advantages in drug discovery application: The N-terminal structure required to express activities of a variety of physiologically active peptides or proteins are maintained; and it is accumulated in the cell maintaining the physiological activities that requires N-terminal, because it has free N-terminal. Then, N-terminal thereof is conveniently modified to bind a variety of substances, thereby the liposome of the cell membrane is modified with them.

EXAMPLE (Example 1) Preparation of the Liposome

The inner solution, the internal fluid of the liposome, and the outer solution, the external fluid of the liposome, are prepared in the composition shown in the following Table 2. Each solution is adjusted to pH 7.5 by using 6N HCl, and then filled up to 50 mL by using milliQ water.

TABLE 2

| Components | Inner solution | Outer solution |
| --- | --- | --- |
| Sucrose | 100 mM | 100 mM |
| Tris (hydroxy)aminomethane-HCl (pH 7.5) | 100 mM | 50 mM |
| NaCl | 50 mM | 50 mM |

The method for preparing the liposome is shown in below.

By using chloroform as the solvent, stock solutions containing 10 mM of 1,2-Dioleoyl-sn-glycero-3-phosphoglycerol (DOPG) and 1,2-Dioleoyl-sn-glycero-3-phosphocholine (DOPC) are respectively prepared as their stock solutions. 50 µL of 10 mM DOPG stock solution or 50 µL of 10 mM DOPC stock solution is respectively placed in a Duhram tube, and then chloroform is removed by spraying nitrogen gas. After that, the Duhram tubes are dried by using a vacuum pump overnight to chloroform sufficiently.

200 µL of liquid paraffine is added into the Duhram tubes taken out from the vacuum vessel, and then they are capped with Parafilm. The tube is applied with ultrasonic wave by using Yamato 3210 for 1 hour to dissolve the lipid, and then, 20 µL of the inner solution to which final concentration 1 µM of fluorescein amin is added to the tube, and then it is vortexed to obtain w/o emulsion in liquid paraffin.

The emulsion is poured into the 1.7 mL of microtube so as to softly load on 200 µL of the outer solution. And then, the tube is stood for stabilizing the interface of the lipid at 4° C. for an hour. After that, the tube is subjected to the centrifugation by using Swing man at about 4,000 rpm for about 10 minutes. Lastly, the w/o emulsion on the upper layer in the tube is removed, and then 50 µL of the liposome solution is collected from the bottom of the lower layer (see, FIG. 6). By the procedure described above, the liposome solution including the different inner solution from the outer solution are obtained.

(Example 2) Construction of the Construct for the Lipid Bilayer Binding Peptide (1) Design of the Construct The construct having the structure shown in FIG. 2D is constructed as follows.

Firstly, the random region is designed based on the sequence which is balanced to have higher arginine content, and appearance ratio of the stop codon is lower in the sequence.

The construct has a concrete constitution: from 5' side to 3' side, histidine tag (HNtag), GGGS region, fluorescent protein gene region, GGGSGGGS (SEQ ID NO: 13) region, random region, and stop codon region (see FIG. 2D). In the fluorescent protein gene region, a gene of mCherry, red fluorescent protein, is incorporated, and the stop codon region is set TGA. The production of the construct is ordered to GeneWorld Inc.

(2) The Sequence of N-Terminal Binding Peptide (LB-1)

The nucleotide sequence to be incorporated as the random sequence is studied based on the amino acid sequence in the random region of the peptide, which binds to the liposome at the N-terminal thereof (LB1), previously obtained by the present inventors (see, FIG. 1(A)).

From the construct, LB1 fusion protein shown in FIG. 1(B) is obtained by using cDNA display method described in below. The liposome prepared in Example 1 and the LB1 fusion protein, the fluorescent protein-labelled protein, are incubated at 25° C. for 3 hours, in which final concentration of the fusion protein is 1 µM, and then it is used as the sample solution. As the reference, the solution containing the liposome alone is incubated at 4° C. for 3 hours. Each solution is observed by using the confocal laser scanning microscope. The observation of the liposome incubated with the fluorescent protein-labelled protein gives a fluorescent microscope image showing the fluorescence is concentrated on the outside of the liposome (see, FIGS. 1(C) and 1(D)). The area to which the fluorescence is concentrated matches that the lipid bilayer of the liposome observed by using the confocal microscope. By this, it is confirmed that the fluorescent protein-labelled protein bounds to the lipid bilayer of the liposome.

Here, the amino acid sequence of LB1 is divided into 5 blocks as A to E in the direction from the N-terminal to the C-terminal (see, FIG. 1(A)). LBP1 contains that the hydrophobic amino acid rich region and the basic amino acid rich region, and these are respectively named as Block B, the hydrophobic amino acid rich region, and Block D, the basic amino acid rich region (see, FIG. 1(A) and the following Table 3).

TABLE 3

| Name | Configuration of the blocks | Amino acid sequence | SEQ ID NO. |
|---|---|---|---|
| LB1 | ABCDE | RHSKSLPSRVIPRADPRTK TRRRRRKRTL | 11 |
| LBPr1 | ErDrCrBrAr | LTRKRRRRRRTKTRPDARP IVRSPLSKSHR | 8 |
| LBPr2 | ADCBE | RHSKSRRRRRKRRTKTLP SRVIPRADPTL | 9 |
| LBPr3 | EDCB A | TLRRRRRRKRRTKTLPSRV IPRADPRHSKS | 10 |

Figure 1C:
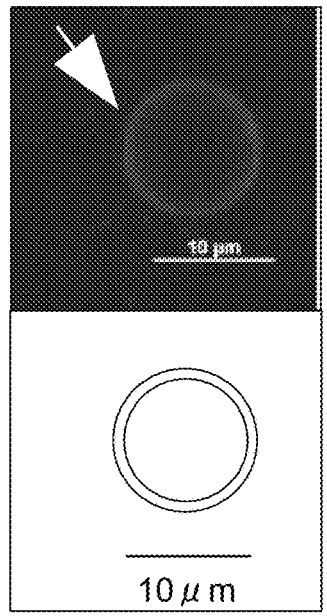
Figure 1D:
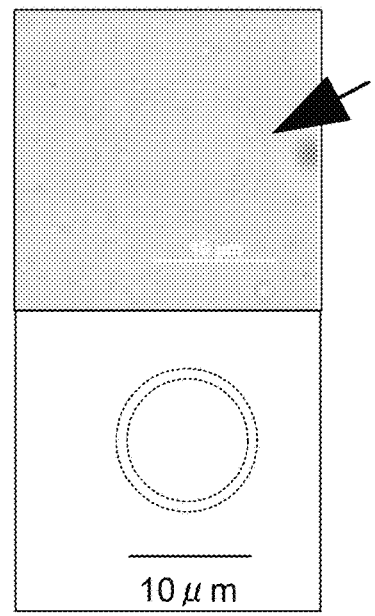

Further to the binding of LB-1 to the liposome, which terminal, either N-terminal or C-terminal is used, it is decided that LB-1 binds to the liposome at N-terminal, because the amino acid sequence of LB-1 has Block B containing the hydrophobic amino acids at N-terminal; and the fluorescent microscope image shown in FIG. 1(C).

(3) Alteration of LB-1

Based on the results as described above, in order to obtain the protein or peptide that bind to the lipid membrane at C-terminal thereof by altering the sequence of LB-1, the amino acid sequence to be incorporated as the random sequence is studied. Firstly, the amino acid sequence of which N-terminal and C-terminal of LB-1 are reversely changed (LBPr1, see, FIG. 2(A) and above table 3) is designed (see FIGS. 2(B) and 2(C), and above table 2). Also, LBPr2 and LBPr3, both of which have replaced block constitution orders of LBP-1 are designed. Then, synthesis of these 3 peptides was ordered to Gene World Inc.

(Example 3) In Vitro Selection by Using cDNA Display Method (1) Synthesis of mRNA By using each construct prepared in Example 2 and T7 RiboMAX Express Large Scale RNA Production System (Promega) is used, and 5 to 30 pmol/µL of mRNA is synthesized according to the protocol as attached thereof.

(2) Formation of the Conjugate, Ligation of mRNA and the Linker

As the linker, cnvK linker is used. cnvK linker (poly A+cnvK) has the biotin fragment in the backbone of poly A+cnvK, and the side chain, and the sequence of SEQ ID NO. 12 of the sequence listing.

[Sequence 12]
5'AAAAAAAAAAAAAAAAAAAAANTTTCCAKGCCGCCCCCCGTCCT3'

Here, BioTEG is bound to 5' terminal of the backbone, and N in the nucleotide sequence shows riboG, and K in that shows cyanovinylcarbasol respectively. Also, puromycin segment, the side chain, has the following sequence.

(SEQ ID NO: 16)
5' (5S)TCTFZZCCP

P is the free terminal of the side chain, and it is puromycin as the protein biding site. In the following nucleotide sequence, (5S) shows 5' Thiol C6, F shows FITC-dT, and Z shows Spacer 18, respectively. The chemical synthesis of the backbone and the side chain was ordered to Tsukuba Oligo Service Co., Ltd.

Firstly, both 15 nmol of the biotin fragment (poly A+cnvK) (final concentration 150 µM) and EMCS (Dojindo Laboratories, final concentration 16.7 mM) are added into 0.2 M sodium phosphate aqueous solution (pH 7.2), and then it is incubated at 37° C. for 30 minutes. Then, by using Quick-Precip Plus Solution (Edge BioSystems), the products are subjected to ethanol precipitation.

Next, 37.5 nmol equivalent puromycin segment is dissolved into 1 M of sodium hydrogen phosphate aqueous solution containing 50 mM DTT so as to become final concentration 417 µM, and then stirred at room temperature for 1 hour by using a shaker. Next, it is loaded on NAP5 for exchanging its buffer to 0.1 M of sodium phosphate buffer (pH 7.0) containing 0.15 M of NaCl.

The reduced puromycin segment solution of which buffer is already exchanged is mixed with the ethanol precipitate of the biotin-fragment (poly A+cnvK) modified with EMCS, and the mixture is stood at 4° C. for overnight. Subsequently, DTT is added into the mixture so as to be final concentration 50 mM, and then it is stirred at room temperature for 30 minutes. After that, the mixture is subjected to ethanol precipitation by using Quick-Precip Plus Solution (Edge BioSystems). Obtained ethanol precipitate is dissolved in 100 µL of Nuclease-free water (Nakarai Tesque), and then purified by using HPLC under the following conditions:

A solution: 0.1 M trimethyl ammonium acetate (in ultra-pure water)
B solution: 80% acetonitrile
Program: Composition ratio of A solution and B solution is gradient, 85% of A solution at start is decreased to 5% over 45 minutes.
Flow rate: 1 mL/min.
Fraction: 1 mL Components in each fraction is confirmed by using the fluorescence and UV absorbance (280 nm). The fraction from 30 to 32 minute showed peaks both of fluorescence and UV. The fractions from 30 to 32 minute are collected, and then the solvent is evaporated by using vacuum evaporator. After that, the evaporated products are subjected to the ethanol precipitation by using Quick-Precip Plus Solution, and then the precipitates are dissolved in Nuclease-free water and stored at −20° C.

At least 30 seconds UV irradiation is sufficient, however, to be on the safe side, it is set about 1 minute. By using RiboMAX Large Scale RNA Production Systems-T7, translation is conducted. mRNA transcribed from the peptide and the cnvK linker (poly A+cnvK) are added to 25 mM Tris-HCl buffer (pH 7.5) containing 100 mM NaCl at final concentration 1 µM, respectively. This mixture is incubated at 90° C. for 1 minute, and then at 70° C. for 1 minute, and then, its temperature is decreased at the ratio of 0.08° C./second to 25° C. for binding puromycin linker (poly A+cnvK) to 3' terminal of mRNA to obtain the mRNA-linker conjugate.

(3) Screening by Using cDNA Display Method (3-1) Cell Free Translation System

As the cell free translation system, Retic Lysate IVT Kit (Ambion) is employed. Methods such as mixing and the like are conducted according to the protocol attached to the kit. All of reagents used in the cell free translation are gently stirred, and then it is centrifuged and placed on an ice. The reaction solution of 25 µL scale is prepared by mixing those in the following order, and then the reaction is conducted: 0.625 µL 20 X Translation Mix minus-Met, 0.625 µL 20 X Translation Mix minus-Leu, and 17 µL of Retic lysate are carefully mixed by using the pipet not to make foam.

The mixture is added to 36.5 µL of the sample solution, and then DEPC water is added to the volume of the reaction mixture to be 25 µL. Then, it is gently mixed without making foam. After the mixing, it is translated at 30° C. for 20 minutes. After the translation reaction, in order to accelerate the ligation between the conjugate A and the synthesized protein, 20 µL of 3M KCl, and 6 µL of 1 M $MgCl_2$ are added to the reaction mixture, and reacted at 37° C. for 40 minutes.

(3-2) Purification of the Peptide

When 90 pmol equivalent cDNA display molecules are present in the solution, 60 µL of amount of the magnetic beads (Dynal, Dynabead MyOne C1) is added to the solution. Then, the solution is incubated at room temperature for 20 minutes to prepare the conjugate to which the synthesized peptide is bound to puromycin of the linker (linker-mRNA-peptide conjugate), and the conjugate is bound to the magnetic beads surface with the linker portion thereof. Note that here used the linker to which the fluorescent protein (GFP) is bound. Next, reverse transcription of mRNA bound to the conjugate is conducted by using ReverTra Ace (TOYOBO) under the conditions of at 42° C. for 30 minutes to obtain cDNA ligated conjugate, the linker-mRNA-peptide-cDNA conjugate. Subsequently, the cDNA-ligated conjugate, cDNA display, is released from the magnetic beads by using RNase T1 at 37° C. for 10 minutes reaction condition.

As described above, LBPr1 to LBPr3 are obtained by using cDNA display method.

(Example 4) Obtaining the LBPr1 Fusion Protein, mCherry-LBPr1

(1) Discovery of LBPr1 Fusion Protein

Freeze-stocked competent cells, BLL21(DE3), are thawed on the ice. 50 µL of the competent cell solution and 1 µL of plasmid solution (DNA concentration from 1 µg to 10 µg) are added into 1.7 mL of the microtube, and then the microtube is stood on the ice for 20 minutes. The microtube is given heat shock at 42° C. for 45 seconds, and then it is stood on the ice for 3 minutes. Then, 400 µL of SOC medium is added into the microtube, and then it is cultured with shaking at 37° C. for 1 hour. After the shaking culture, 100 µL of the competent cell solution is plated on LB agar plate supplemented 100 µg/mL of ampicillin, and then the plate is incubated at 37° C. for 18 hours.

After the incubation, formed E. coli colonies are picked-up and added into 1.5 mL of LB medium supplemented with 100 µg/mL of ampicillin, and then cultured with shaking at 37° C. for 18 hours. After the shaking culture, by using shaking flasks with baffles, the culture volume is scale-up to 100 mL, and then cultured with shaking at 28° C. for 4 hours. After 4 hour shaking culture, IPTG is added at final concentration 1 mM to the culture medium, and then cultured with shaking at 28° C. for 20 hours to induce the expression of the protein, mCherry-LBPr1.

(2) Purification of LBPr1 Fusion Protein

Preliminary, two centrifuge tubes of 50 mL size are weighed. Then, 50 mL portion of the culture medium obtained in Example 4 is added into each centrifuge tube, and the tubes are centrifuges in 2,000×g for 5 minutes. After the centrifugation, supernatant is discarded and the precipitate, E. coli, are weighed. 5 mL of Bugbuster is added to E. coli per 1 mg, and then suspended without making foam. Thirty minutes later, the solution is gently shaken at room temperature for bacteriolysis. After that, the solution is centrifuged in 14,000×g for 20 minutes, and the solution containing protein is recovered in 1.7 mL of the microtube.

After that it is subjected the purification by using coordination bond between histidine and Ni-NTA (His-tag purification). Two buffer compositions used for the purification are shown in Table 2 in below. PBS (−) shows phosphate buffered physiological salt solution (phosphate-buffered saline), and (−) means that $Ca^{2+}$, and $Mg^{2+}$ are not contained in the solution.

TABLE 4

| Components | Washing buffer | Elution buffer |
|---|---|---|
| Phosphate | 20 mM | 20 mM |
| NaCl | 500 mM | 500 mM |
| Imidazole | 20 mM | 250 mM |

The protocol pf His-tag purification is as follows. Firstly, 1 mL of Ni-NTA agarose is packed in Poly-Prep (a registered trademark) chromatography column, which is simply described as a column, and equilibrated with 3 mL of PBS(−). The solution containing the protein extracted from E. coli obtained in Example 4 is loaded. Ten mL of washing buffer is added to the column to wash out the protein other than mCherry-LBPr1, and the like. Then, 1 mL of elution buffer is added to the column to elute and recover mCherry-LBPr1 into 1.7 mL of the microtube.

Furthermore, by using the same procedure, both mCherry-LBPr2 protein and mCherry-LBPr3 protein are respectively produced and purified.

(Example 5) Reaction Between Each of the Fusion Protein (mCherry-LBPr1, mCherry-LBPr2 and mCherry-LBPr3)

(1) Preparation of the Liposome Solution (DOPC)

In order to obtain the solution containing the liposome of which inner solution is different from outer solution, the liposome inner solution which has contains the composition shown in Table X1 of Example 1 and supplemented with 1 µM fluorescein amine, a green fluorophore; and the liposome outer solution which contains 0.1 M glucose, 100 mM tris-HCl (pH 7.5) and 50 mM NaCl are respectively prepared.

200 µL of liquid paraffin mixture containing 50 µL of 10 mM phospholipid, 1,2-dioleoyl-sn-glycero-3-phosphocholine (DOPC) is poured into the centrifuge tube. Then, the liposome inner solution is layered and then vortexed to prepare the liposome containing the liposome inner solution.

Thus obtained liposome containing solution is gently poured on the liposome outer solution and stood at 4° C. for 1 hour. Then, it is centrifuged in 3,000 round/minute to transfer the liposome into the liposome outer solution to prepare the liposome solution of which inner solution and the outer solution are different, hereinbelow, it is referred to as "DOPC".

(2) Reaction Between Each Fusion Protein, mCherry-LBPr1, mCherry-LBPr2 and mCherry-LBPr3

Any one of the purified mCherry-LBPr1, mCherry-LBPr2, and Cherry-LBPr3 obtained in Example 4 is added into DOPC at final concentration 1 µM, and thus obtained solution is reacted at 4° C. for 3 hours by using a cooling type thermo-block rotator (SNP-24B). After termination of the reaction, the binding of each fusion protein to the liposome is observed by using the confocal laser scanning microscope and flow cytometer.

The incubation results of mCherry-LBPr1 and the fusion protein are as follows. In the fluorescent observation, before starting of the incubation, red fluorescent detection showed that red color is located in the outer solution wherein the fusion protein is contained, and the liposome filled with the inner solution containing the fusion protein is detected as a black spherical shape. Also, the green fluorescence detection showed that the liposome outer solution which does not contain fluorescein amine is dark, and the liposome is a green spherical shape.

After finishing the incubation, the red fluorescent detection could not detect the shape of the liposome, and this indicates that mCherry-LBPr1 is penetrates the lipid bilayer of the liposome. Also, the green fluorescence detection revealed that there is almost no leakage of the liposome inner solution into the outer solution. Therefore, it is clarified that mCherry-LBPr1 transferred into the liposome without forming pores in the lipid bilayer of the liposome.

Figure 7A:
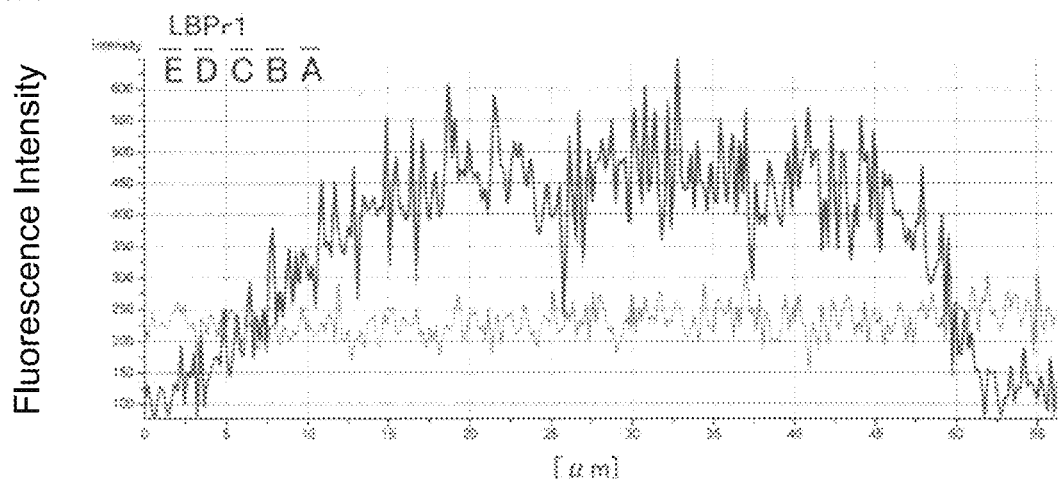
FIG. 7(A) to (C) shows the observation results of the interaction after incubation of mCherry-LBPr1, mCherry-LBPr2, and mCherry-LBPr3 with the liposome by using the confocal laser scanning microscope. In the figures, alphabets A to E indicate the blocks shown in FIG. 1(C), and the alphabets with bars in FIG. 7(A), which is corresponding to Er, Dr, Cr, Br, and Ar in the specification, show that the amino acids composing the blocks are arranged reverse orders.
Figure 7B:
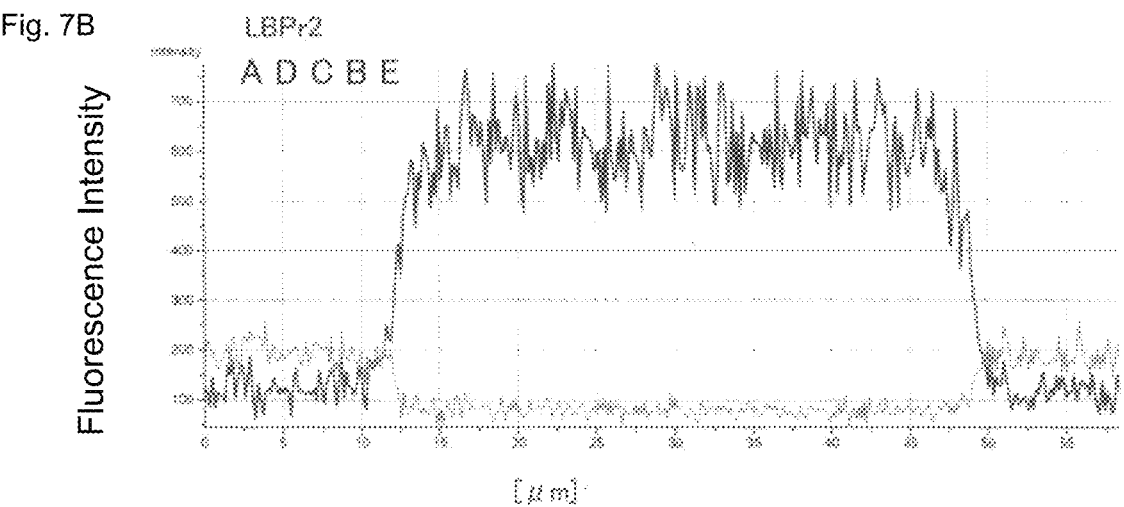
Figure 7C:
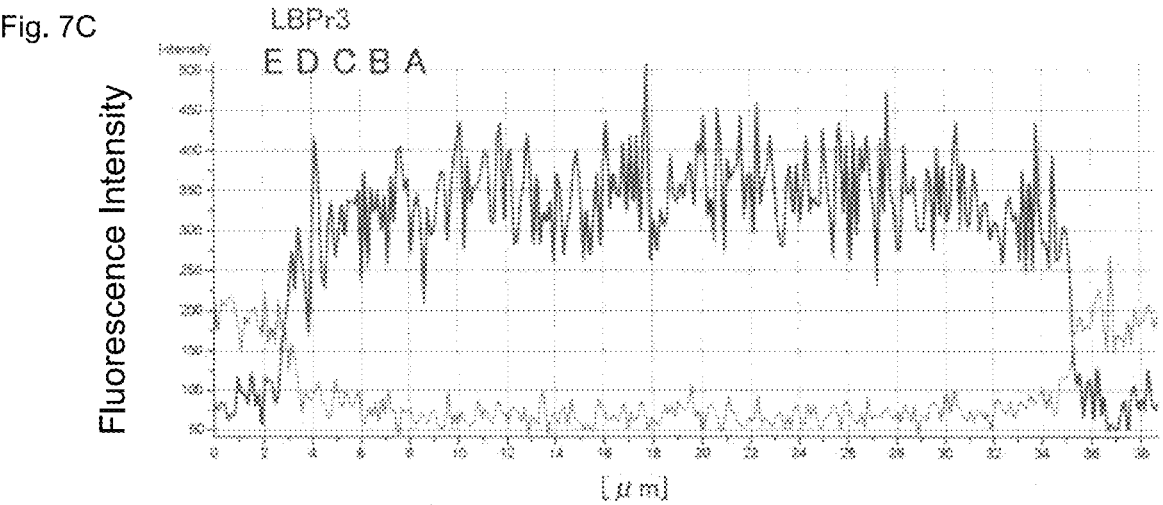

In contrast, when either of mCherry-LBPr2 or mCherry-LBPr3 and DOPC are incubated, the liposome is observed as the black spherical shape even if the termination of the incubation. By this, these do not transfer into the liposome. Observation results by using the flow cytometer are shown in FIGS. 7(A) to 7(C).

Figure 3:
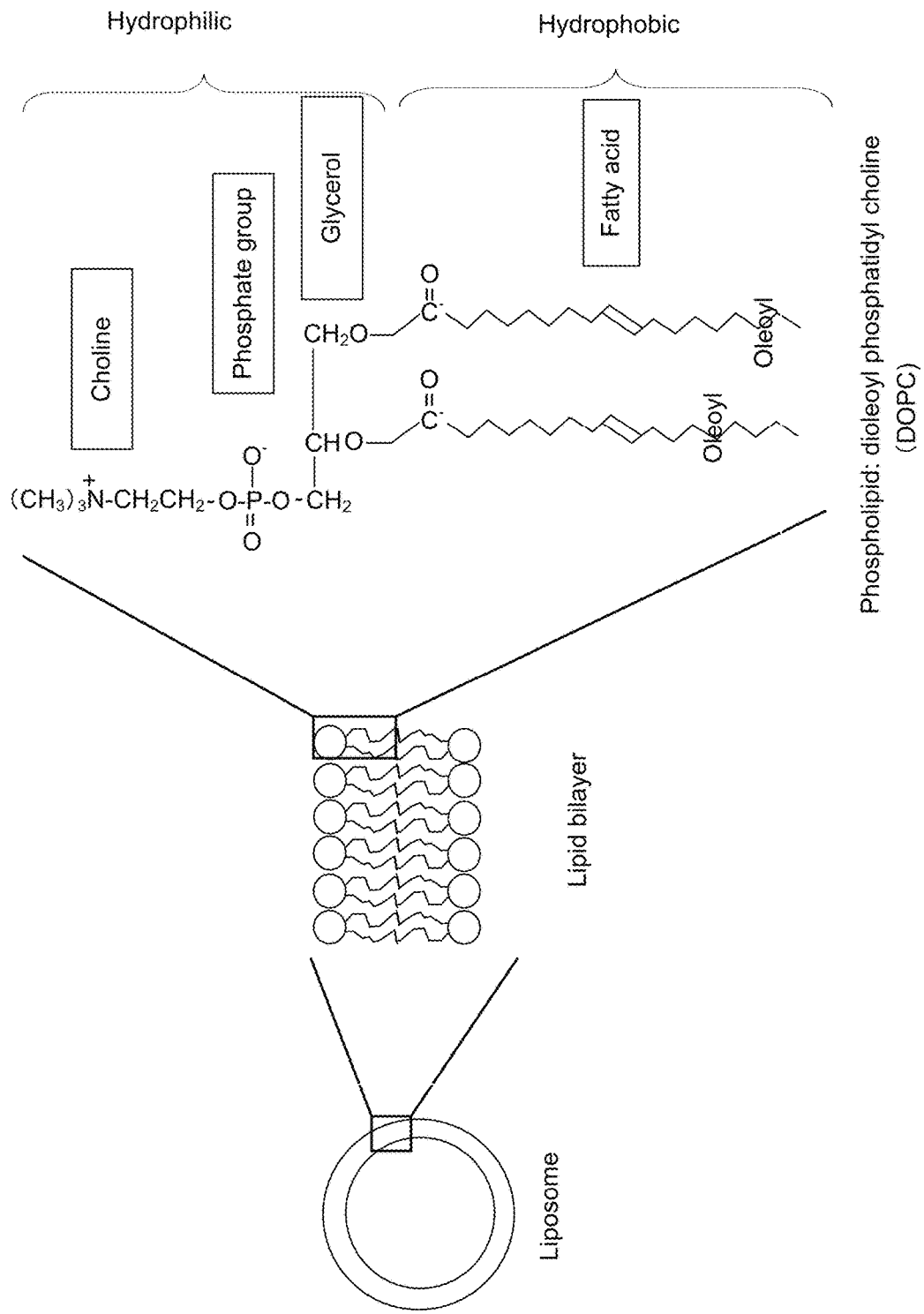
FIG. 3 is the schematic figure showing the liposome structure as a model of a bio membrane.

(3) Change of the Penetration LBPr1 Depending on the Fused Fluorescent Protein Thereof Instead of mCherry in the construct shown in FIG. 3, GFP-LBPr1 is prepared by ordering to GeneWorld Co., Ltd. Also, final concentration 1 µM of mCherry is added to the inner solution of the liposome, final concentration 1 µM of GFP is added to the outer solution of the liposome. Then, the liposome solution containing the different inner solution and outer solution is prepared by using the same method as described above, and the penetration of GFP-LBPr1 of the lipid bilayer is studied.

The results shown in FIG. 8(A) to FIG. 8(B). At the start of the incubation, the liposome was detected as the black spherical shape. However, at the end of incubation, the color thickness of the spherical shape showing the liposome became rather light. Therefore, it indicated that GFP-LBPr1 is incorporated inside of the liposome, DOPC.

Figure 9:
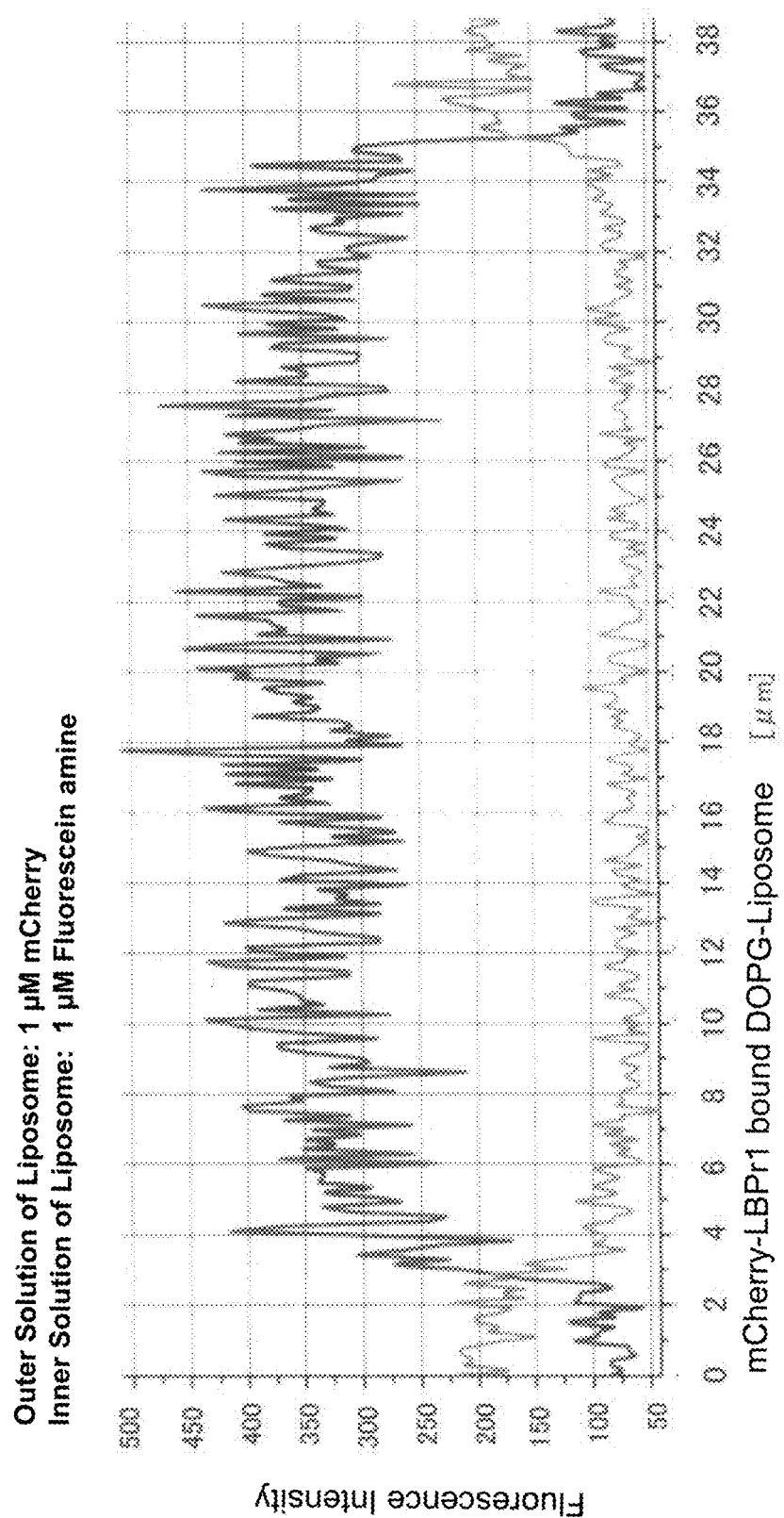
FIG. 9 shows the observation results of the change when the liposome solution (DOPG) and mCherry peptide are incubated by using the confocal laser scanning microscope (Olympus Corporation).
Figure 11A:
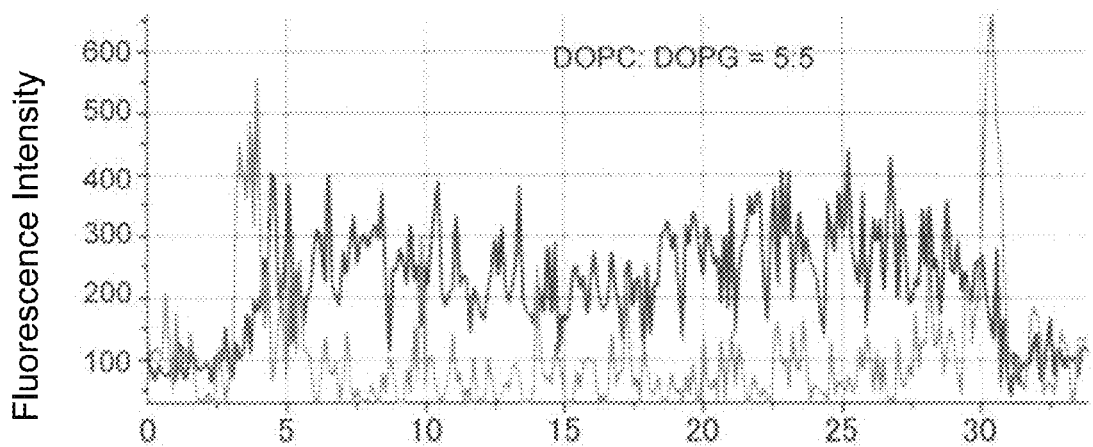
FIG. 11(A) to (C) shows the change of the mixed liposome, which is manufactured by mixing DOPG and DOPC at different ratio, after incubating with and mCherry-LBPr1 by using the confocal laser scanning microscope (No. 1).
Figure 11B:
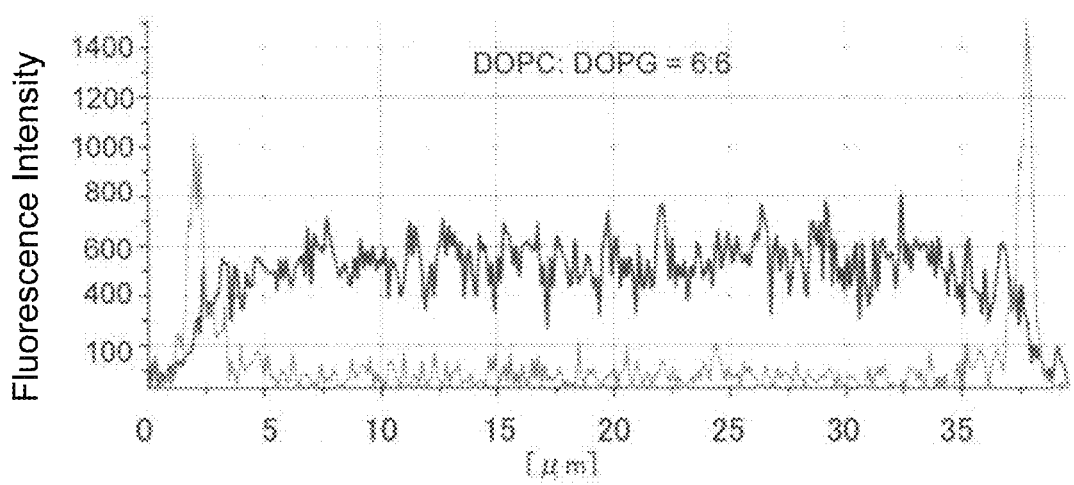
Figure 11C:
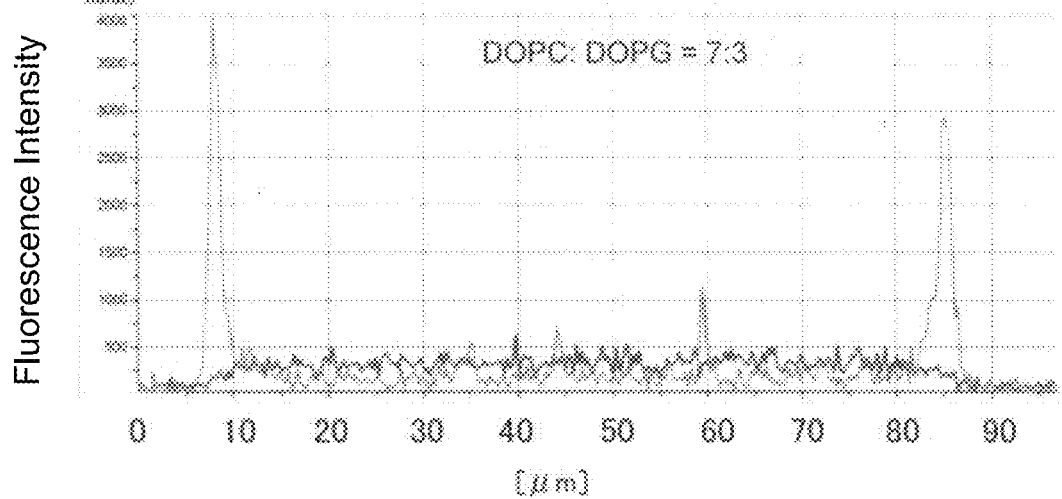
Figure 12A:
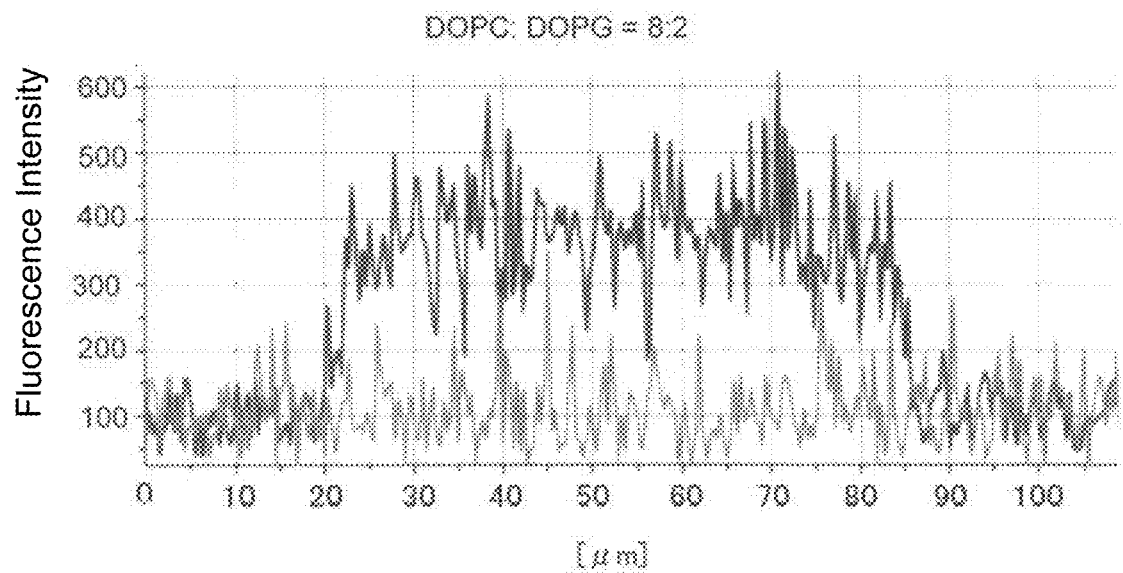
FIG. 12(A) to (B) shows the change of the mixed liposome, which is prepared by mixing DOPG and DOPC at different ratio, after incubating with and mCherry-LBPr1 by using confocal laser scanning microscope (No. 2).
Figure 12B:
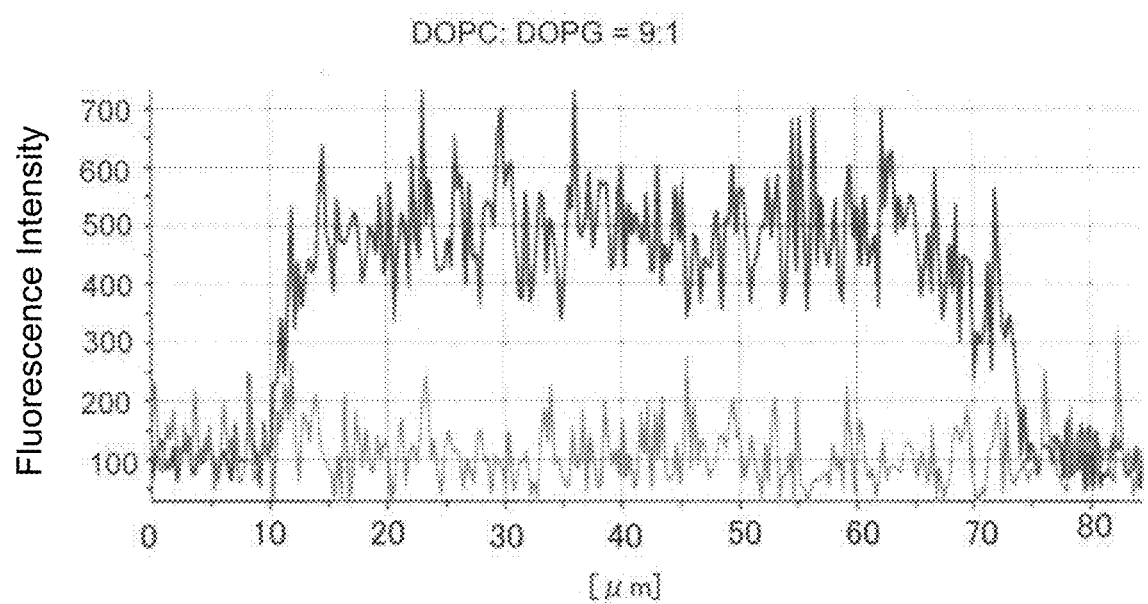

(4) Change of the Interaction Between LBPr1 and the Liposome Depending on the Composition Thereof Change of the interaction of the liposome and mCherry-LBPr1 is studied by using sodium 1,2-dioleoyl-sn-glycero-3-phospho-rac-(1-glicerine), DOPG as the phospholipid. As the control, the liposome outer solution containing mCherry peptide is used. Results are shown in FIG. 9 and FIG. 10. From the results, it is demonstrated that mCherry-LBPr1 was bound to the surface of the liposome (DOPG), but it was not incorporated in the liposome.

Next, the liposomes are prepared by using the mixture of DOPG and DOPC. Mix ratios of DOPG:DOPC=5:5, 6:4, 7:3, 8:2, 9:1. The mixed liposomes formed by DOPG and DOPC are reacted with mCherry-LBPr1 as described above. Results are shown in FIG. 11(A) to FIG. 12(B).

From the results, it is demonstrated that the ratio of DOPG:DOPC of the liposome is equal to or over 7:3, mCherry-LBPr1 does not penetrates the liposome membrane, but binds to the surface thereof. Namely, the ratio of DOPG becomes higher, mCherry-LBPr1 cannot penetrate the lipid bilayer of the liposome.

(Example 6) Interaction Between HeLa Cell and mCherry-LBPr1

(1) Cell Assay

In DMEM (−) or PBS (−), HeLa cells and mCherry-LBPr1 are contacted to study that the cell is used instead of the liposome.

TABLE 5

| No. | Buffer used | Protein added |
|---|---|---|
| Sample 1 | DMEM(−) | mCherry-LBPr1 |
| Sample 2 | PBS(−) | mCherry-LBPr1 |
| Sample 3 | DMEM(−) | mCherry-LBPr1 |
| Sample 4 | PBS(−) | mCherry |
| Control 1 | DMEM(−) | None |
| Control 2 | PBS(−) | None |

In Table, DMEM indicates Dulbecco's Modified Eagle Medium (Dulbecco's Modified Eagle Medium), the symbols, (+) and (−), indicate the presence or absence of 10% (v/v) fetal bovine serum, FBS, in the medium. EDTA is an abbreviation of Ethylenediaminetetraacetic acid (Ethylenediaminetetraacetic acid), and EDTA/PBS (−) indicates that EDTA is diluted with PBS (−). Also, trypsin/PBS (−) indicates that trypsin is diluted with PBS (−).

In TPP tissue culture flask (25 cm$^2$) containing DMEM (+), Hela cells are cultured, and the culture supernatant is removed by using an aspirator. Next, 1 mL of 0.2 mM EDTA/PBS (−) is added to the flask, and then the flask is stood at room temperature for 1 minute to chelate metallic ions in the buffer, and the buffer is removed by using the aspirator. Next, 1 mL of 0.25% (v/v) trypsin/PBS (−) is added to the flask, and then the flask is incubated in 5% $CO_2$ incubator at 37° C. for 3 minutes to release HeLa cells from the flask. After confirmation that HeLa cells are released from the flask, and then 4 mL of DMEM (+) is added into the flask and pipetted.

49 mL of DMEM (+) is added to the flask, and suspended the cells by sufficiently pipetting. Three mL of the cell suspension is poured into 8 poly-D-lysine coat dishes, 35 mm glass bottom, hereinbelow, it is sometimes simply referred to as a "dish", respectively, and then these dishes are incubated in 5% $CO_2$ incubator at 37° C. for overnight. Six dishes among 8 dishes described above, wherein cell are well grown, are chosen, and then, the culture supernatant, DMEM (+), in them is removed by using the aspirator. After that, the following procedure is repeated 3 times: adding 2 mL of DMEM (−) or PBS (−) to fit the observation conditions of the samples, and removing the buffer by using the aspirator, hereinbelow, it is referred to as "washing", to remove DMEM (+) in the dishes.

In order to observe each sample and control, 2 mL of DMEM (−) or PBS (−) is added thereto. 13.8 µL of 1.45 mM mCherry-LBPr1 is added to the dishes containing the sample Nos. 1 and 2, and 244 µL of 81.8 µM mCherry is added to these containing the sample Nos. 3 and 4, all of final concentration are 10 µM. Then, each dish containing either the sample or control are incubated in 5% $CO_2$ incubator at 37° C. for 1 hour. The cells are washed with 2 mL of DMEM (−), and then further 2 mL of DMEM (−) is added to observe them by using the confocal laser scanning microscope.

Figure 13A:
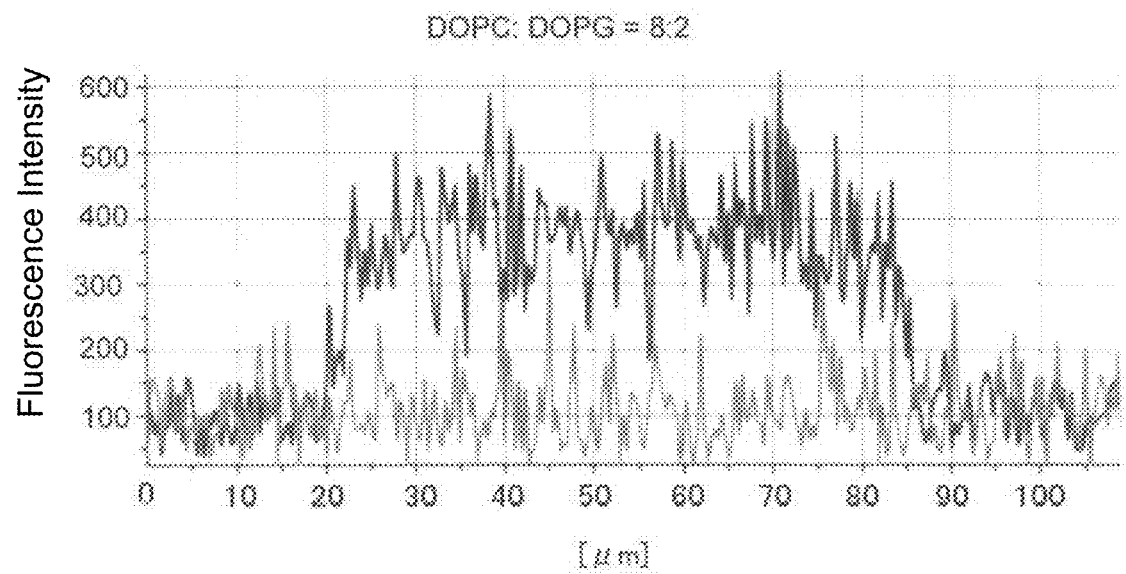
FIG. 13(A) to (B) is the confocal laser scanning microscopic image which shows the result for studying change of the incorporation of mCherry-LBPr1 or mCherry depending when the different solution is used for incubating the cell. In the figure, the cells indicated by arrows are these that showed the incorporation of mCherry-LBPr1.
Figure 13B:
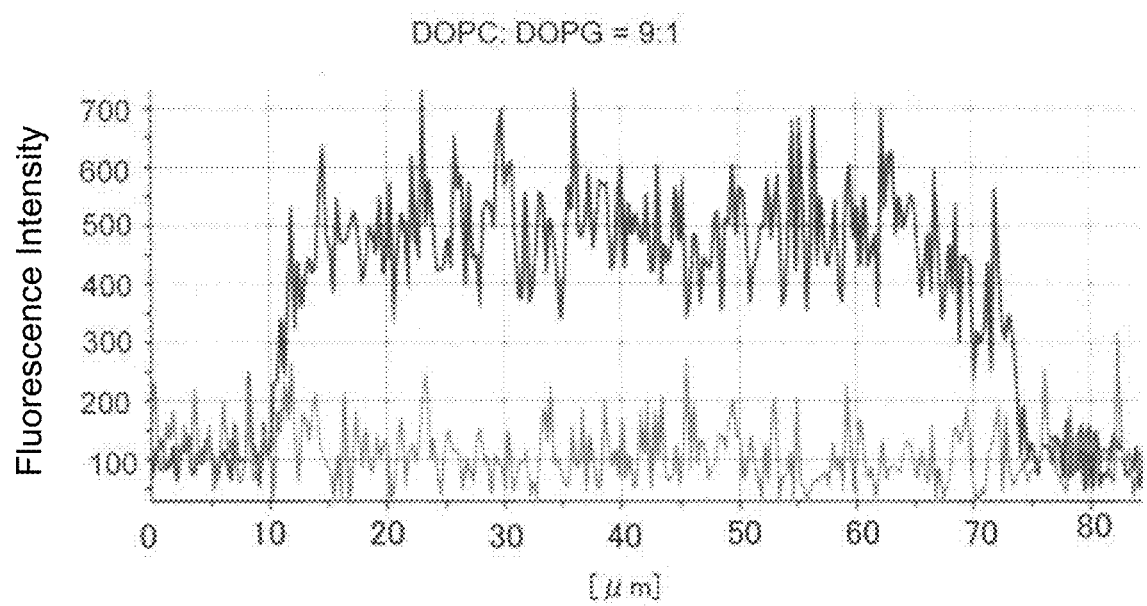

FIG. 13 shows the observation result of the sample after 1 hour incubation by using the confocal microscope. FIG. 13 (A) is the microscope image when either of mCherry only or mCherry-LBPr1 is added to DMEM (−), FIG. 13 (B) is that when either of them is added to PBS (−). Arrows indicate the cells having red fluorescence.

When mCherry-LBPr1 is added, in either case that DMEM (−) or PBS (−) is used, the localization of red fluorescence in the cell is observed, however, it is not observed when mCherry is added. From this, it was confirmed that mCherry-LBPr1 penetrates the lipid bilayer by 1 hour incubation as the same as that mCherry-LBPr1 is interacted with the liposome.

(Example 7) Functions of mCherry-LBPr1 in the Cell Assay (1) Cell Assay

The cell assay is conducted by using either of DMEM (−) or PBS (−), and mCherry-LBPr1 incorporation into HeLa cells are confirmed by using the flow cytometer.

TABLE 6

| No. | Protein added | Incubation time (min.) |
|---|---|---|
| Sample 1 | mCherry-LBPr1 | 15 |
| Sample 2 | mCherry-LBPr1 | 60 |
| Sample 3 | mCherry-LBPr1 | 120 |
| Sample 4 | mCherry | 15 |
| Sample 5 | mCherry | 60 |
| Sample 6 | mCherry | 120 |
| Control 1 | None | 120 |

HeLa cells are cultured in TPP tissue culture flask (25 $cm^2$) containing DMEM (+), and then the culture supernatant is removed by using the aspirator. Next, 1 mL of 0.2 mM EDTA/PBS (−) is added to the flask, and stood at room temperature for 1 minute to chelate the metallic ions in the buffer. Then, the buffer is removed by using the aspirator. 1 mL of 0.25% (v/v) trypsin/PBS (−) is added to the flask and then the flask is incubated in 5% $CO_2$ incubator at 37° C. for 3 minutes to release the cell from the flask. After the confirmation that the cells are released from the flask, 4 mL of DMEM (+) is added and then fully pipetted to transfer the 50 mL sized centrifuge tube. After that, further 14 mL of DMEM (+) is added to the tube and pipetted to prepare the cell suspension.

Thus prepared cell suspension is centrifuged in 1,000 rpm for 1 minute, and the supernatant is removed by using the aspirator. Another 14 mL of DMEM (+) is again added and then pipetted, and then, 1 mL of the suspension is poured into each well of 12 well TPP tissue culture plate. In each well, another 1 mL of DMEM (+) is added, and then the plate is incubated in 5% $CO_2$ incubator at 37° C. for 2 days. The culture supernatant of each well is removed by the aspirator, and the wells are washed with 400 µL of DMEM (−) for 3 times, and then 400 µL of DMEM (−) is added to each well.

In order to adjust the protein to be added to set the final concentration of 10 µM, 0.6 µL of 6.72 mM mCherry-LBPr1 is respectively added to the sample No. 1 to 3; and 0.84 µL of 4.77 mM mCherry is respectively added to the sample No. 4 to 6. The sample Nos. 1 to 6 to which the proteins are added are incubated in 5% $CO_2$ incubator at 37° C. for 15 minutes, 1 hour, or 2 hours together with controls. After that, they are washed with 500 µL of DMEM (−) for 3 times, and then, 250 µL of 0.2 mM EDTA/PBS (−) is added to them, and stood at room temperature for 1 minute to recover the supernatant.

250 µL of Accutase and Accumax is respectively added to the recovered solution, the supernatant in the wells of the plate, and then incubated in 5% $CO_2$ incubator at 37° C. for 3 minutes to release the cells from the plate to recover them. 250 µL of 0.25% (v/v) trypsin/PBS (−) is added to each well of the plate. Then, the plate is incubated in 5% $CO_2$ incubator at 37° C. for 3 minutes to release the cells remained in the wells. After that, 500 µL of PBS (−) is poured into each well, the cells released by the above procedure is recovered. The cell suspension recovered as described above is collected per well, in total amount 1.5 mL, and then transferred into the 15 mL sized centrifuge tube. The tubes are centrifuged in 1,000 rpm for 2 minutes, and then the supernatant is discarded. The precipitated cells are washed twice with 1 mL of PBS (−), and then 1 mL of PBS (−) is added to them to transfer the entire of the content amount in the centrifuge tube in 1.7 mL of the microtube, respectively.

(2) Observation Results by FACS

Immediately before FACS measurement, the cells are mutually separated by using Cell strainer, and then they are measured as quickly as possible. Results are shown in FIG. 14 and Table 7 in below.

TABLE 7

| Incubation time | Uptake of the added protein (%) | |
|---|---|---|
| (min.) | mCherry | mCherry-LBPr1 |
| 15 | 0.87 | 7.12 |
| 60 | 1.32 | 84.90 |
| 120 | 14.24 | 95.42 |

Figure 14:
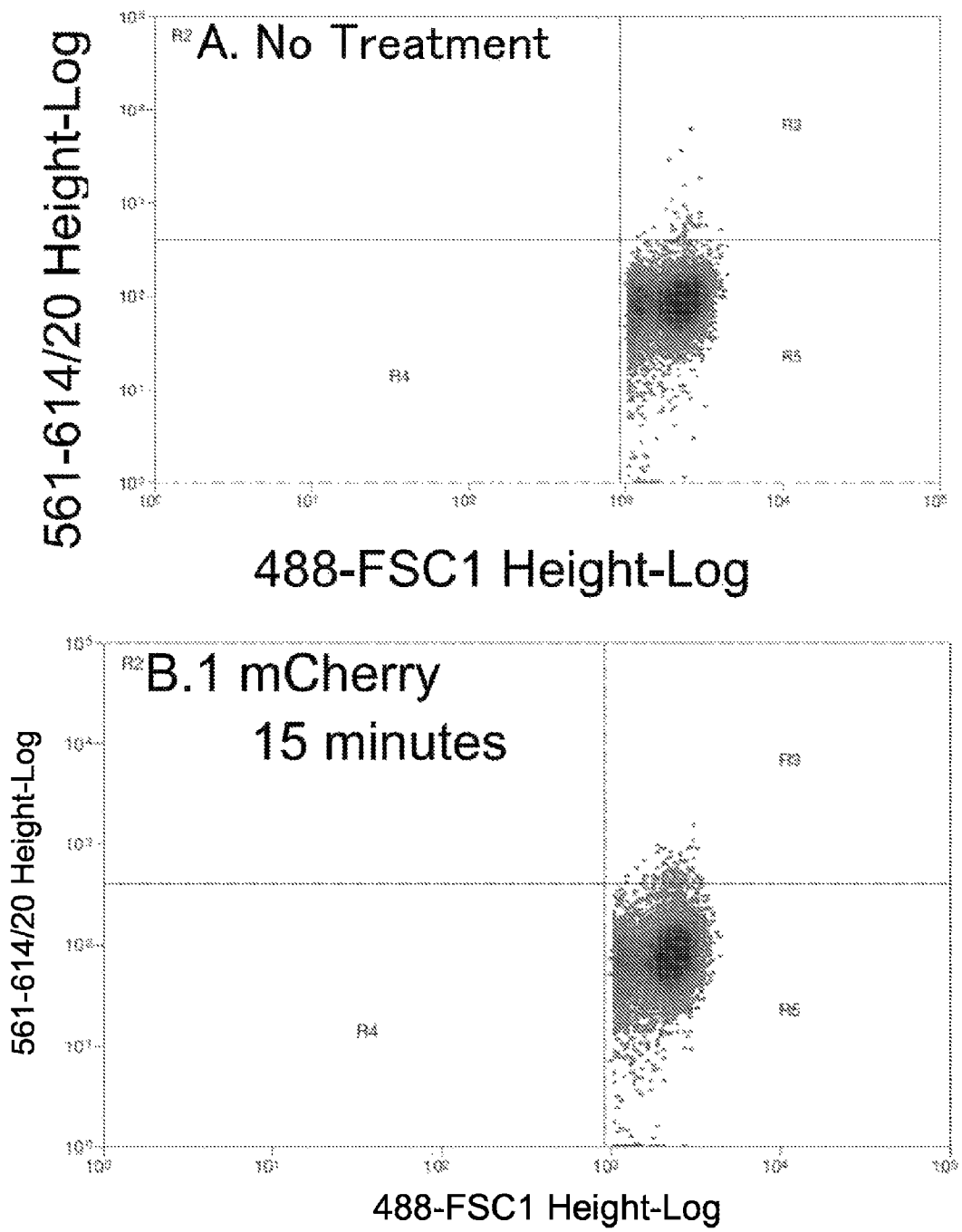
FIG. 14 is the figure showing cell assay result of mCherry-LBPr1 uptake into HeLa cell incubated in DMEM (−) or PBS (−) by using a flow cytometer.

As FIG. 14 clearly shows, in the case that mCherry is simply added, FACS images did not show large change from 15 minutes to 120 minutes. In contrast, when mCherry-LBPr1 is added, the detected images were time-dependently shifted to upper direction, and this shows that uptake of them into HeLa cells occurred. As shown in Table 7 above, the uptake efficiency of mCherry-LBPr1 reached about 85% within 1 hour, and over 95% at 2 hours.

From the above, it was confirmed that mCherry-LBPr1 penetrates the cell membrane of HeLa cells as the same as that occurred in the liposome.

(Example 8) Study of mCherry-LBPr1 Localization in the Cells

Organelles in the cell are labelled, and then mCherry-LBPr1 acts to HeLa cells in DMEM (−). As the labeling reagents, Hoechest 33342 (Dojindo laboratories) for a nucleus, CellLight (the registered trademark), Early Endosomes-GFP (Thermofisher Scientific) for early endosome, and CellLight Late Endosomes-GFP (ditto) for late endosome are used. Here, Hoechest 33342/PBS (−) indicates that Hoechest 33342 is diluted with PBS (−) (see, following Table 8).

TABLE 8

| No. | Labelled organelle | Added protein |
|---|---|---|
| Sample 1 | Nuclei & early endosomes | mCherry-LBPr1 |
| Sample2 | Nuclei & early endosomes | mCherry |
| Ssample3 | Nuclei & late endosomes | mCherry-LBPr1 |
| Sample 4 | Nuclei & late endosomes | mCherry |
| Sample 5 | Nuclei | mCherry-LBPr1 |
| Sample 6 | Nuclei | mCherry |

Experiments are conducted as follows. Firstly, HeLa cells are cultured in the flask containing DMEM (+), the culture sup is removed by using the aspirator. 1 mL of 0.2 mM EDTA/PBS (−) is added to the flask, which is stood at room temperature for 1 minute to chelate the metallic ions in the buffer. Then, the buffer is removed by using the aspirator, 1 mL of 0.25% (v/v) trypsin/PBS (−) is added to the flask, and then incubated in 5% $CO_2$ incubator at 37° C. for 3 minutes to release the cells from the flask. After confirmation that the cells are released from the flask, 4 mL of DMEM (+) is added, and then pipetted to prepare the cell suspension. Next, 24 mL of DMEM (+) is further tot added to the cell suspension, and fully pipetted.

Thus obtained cell suspension is poured into 8 dished at 3 mL per dish, and then the dishes are incubated in 5% $CO_2$ incubator at 37° C. for overnight. Four dishes among 8 dishes described above, wherein the cells are well grown, are chosen. After that, 100 µL of CellLight Early Endosomes-GFP is added to both dishes containing the sample 1 or 2, as well as 100 µL of CellLight Late Endosomes is added to both dishes containing the sample 3 or 4, and then, these dishes are incubated in 5% $CO_2$ incubator at 37° C. for overnight to label endosome.

As described above, the cells of the sample Nos. 1 to 4 treated with the labelling agent, and these of the sample Nos. 5 and 6 are respectively transferred into the dishes. 2 mL of Hoechest 33342/PBS(−) (5 µg/mL) is added to each dish, and then they are incubated in 5% $CO_2$ incubator at 37° C. for 10 minutes to label the nucleus. After the termination of the incubation, the cells in each dish are washed with 3 mL of DMEM (−) to remove unreacted Hoechest 33342. After that, 2 mL of DMEM (−) is added to each dish.

In order to adjust the final concentration of the added protein to 10 µM, 628 µM mCherry-LBPr1 is added to the dishes containing any one of the sample Nos. 1, 3, and 5, and 479 µM mCherry is added to the dishes containing any one of the sample Nos. 2, 4, and 6. Next, the dishes containing these samples are incubated in 5% $CO_2$ incubator at 37° C. for 2 hours. After the termination of the incubation, each dish is washed with 2 mL of DMEM(−), and then 2 mL of DMEM(−) is added. The dishes containing each sample is observed by using the confocal laser scanning microscope.

Figure 15:
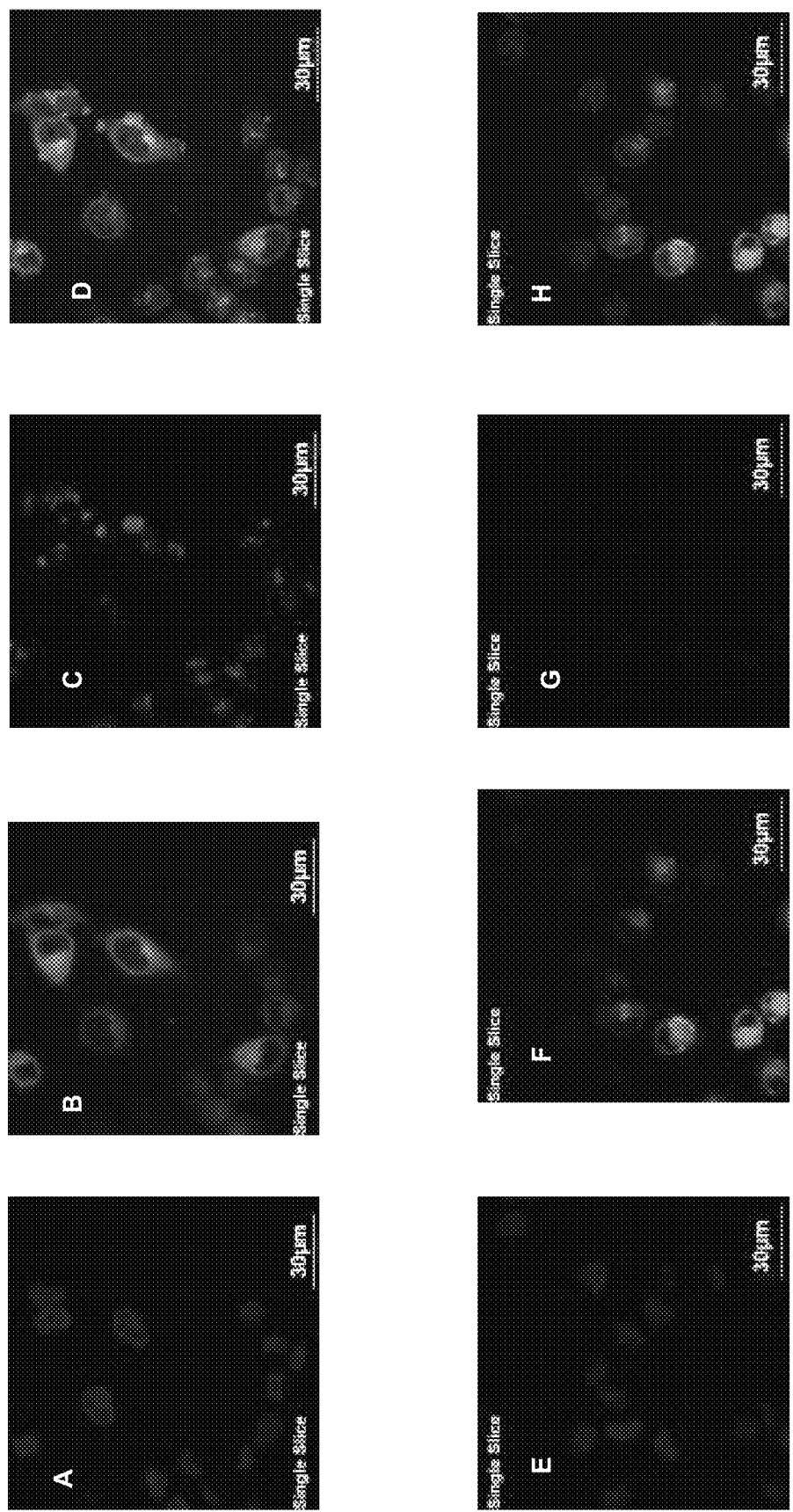
FIG. 15 is the fluorescent observation image showing the localization of mCherry-LBPr1 penetrated the cell membrane by fluorescent labelled organelles, which are early endosome and nuclei.
Figure 16:
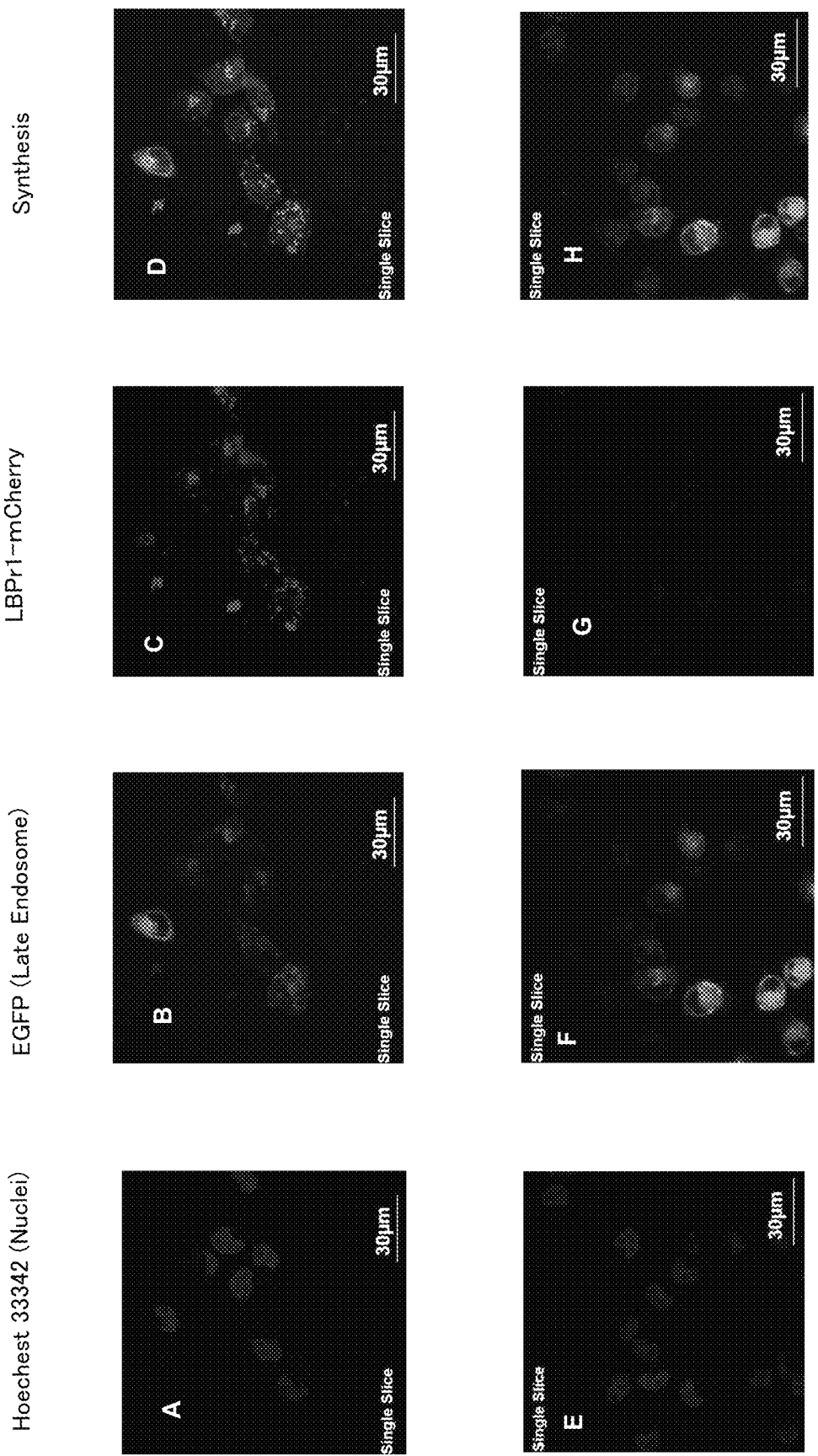
FIG. 16 is the fluorescent observation image showing the localization of mCherry-LBPr1 penetrated the cell membrane by fluorescent labelled organelles, which are late endosome and nuclei.

Results are shown in FIGS. 15 and 16. As shown in FIG. 15, mCherry-LBPr1 does not localized in the nuclei of HeLa cells, but localizes in early endosome thereof. Also, as shown in FIG. 16, mCherry-LBPr1 localizes in late endosome of HeLa cells.

From the above, it is clarified that mCherry-LBPr1 detected by red fluorescent co-localizes endosome which is detected by green fluorescence. This indicates that mCherry-LBPr1 is incorporated in Hela cells with an endocytosis. Therefore, it was shown that LBPr1 is CPP having the property to penetrate the liposome membrane.

(Example 9) Construction of a Construct for Different Lipid Bilayer Binding Peptide (mCherry-R8)

(1) Design of the Construct

From the above experiments, it is unexpectedly shown that LBPr1 is the cell membrane penetrating peptide. As the cell penetrating peptide, which is referred to as "CPPs", for example, TAT protein or R8 peptide, which is the peptide composed of R8 Arginine are known. Hereinbelow, it is abbreviated to "R8". Then, as shown in FIG. 5, the construct to which R8 peptide incorporated instead of LBPr1, R8 peptide is designed.

(2) Synthesis of mCherry-R8 by Inverse PCR

As the template, mCherry-LBPr1 is used. The half sequence of mCherry-LBPr1 from C-terminal to the center is incorporated into one DNA strand of the pET21α vector, and the complementary strand of mCherry-LBPr1 is incorporated to another DNA strand of the pET21α vector.

This PCR is conducted by using a primer with R8, and then PCR product comprising R8 instead of LBPr1, namely, mCherry-R8 is obtained (see, FIG. 6). (Primer used and PCR conditions are required).

(Example 10) Comparison of mCherry-LBPr1 and mCherry-R8

Penetration of the liposome (DOPC) is compared by using mCherry-R8, mCherry-LBPr1, and mCherry only obtained in Example 9.

The inner solution of the liposome is prepared by using the inner solution shown in Table 2 supplemented with 1 µM fluorescein amine. Also, the outer solution of the liposome is prepared by using 0.1 M glucose, and 100 mM Tris-HCl buffer (pH 7.5) containing 50 mM NaCl supplemented with 1 µM mCherry.

The DOPC liposome solution of which inner solution is different from the outer solution is prepared according to the procedure shown in Example 5. Then, one protein selected from the group consisting of mCherry only, mCherry-LBPr1, and mCherry-R8 is added to the liposome solution, and then it is incubated. After that, membrane penetration thereof is compared by using the confocal laser scanning microscope and FACS. Results are shown in FIG. 17.

As shown in FIG. 17(A), when sole mCherry is added, the liposome is detected as a spherical shape shadow, which is darker red than that of the outer solution. The fluorescent spectrum of it showed that both edges are higher and the center is lower. Therefore, it showed that mCherry is localized in the outer solution, but it did not localize in the inner solution, namely, the peptide did not penetrate the membrane.

When mCherry-R8 is added to the liposome solution (see, FIG. 17(B)), the liposome is detected as the spherical shape shadow, darker red color than the outer solution, and there was almost no difference from that the case of sole mCherry addition. In contrast, when mCherry-LBPr1 is added (see, FIG. 17 (C)), the liposome is not detected. From the fluorescence spectrum, the tendency that the center of the spectrum of the liposome becomes lower is disappeared. It indicated that mCherry-LBPr1 penetrates the liposome membrane.

Figure 18:
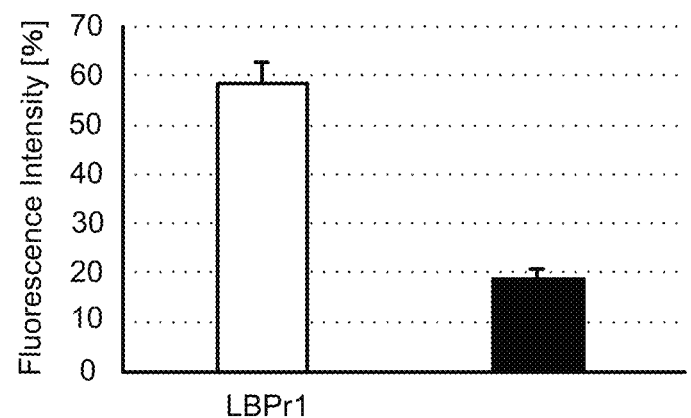
FIG. 18 is the graph showing the comparison result of the fluorescent intensity of mCherry, mCherry-LBPr1, and mCherry-R8.

The ratios of the fluorescence intensity between inside and outside of the liposome, the fluorescence intensity inside of the liposome/the fluorescence intensity of the outside of the liposome x 100, are calculated for mCherry-R8 and mCherry-LBPr1 (n=10). As a result, as shown in FIG. 18, the ratio of mCherry-LBPr1 showed about 3 times higher than that of mCherry-R8.

From the above, for DOPC liposome, both hydrophobic amino acids and basic amino acids in mCherry-LBPr1 contribute to the membrane penetration thereof.

INDUSTRIAL APPLICABILITY

The present invention is available in wide range of fields such as pharmaceutical agents, diagnostic agents, environmental analysis, food analysis, bio-imaging for research, and the like.

FREE TEXT OF SEQUENCE LISTING

SEQ ID NO. 1: Amino acid Sequence of Block Br having the reverse sequence of Block B in the liposome interacting peptide, which interacts with the liposome at C-terminal.

SEQ ID NO. 2: The Amino acid Sequence of Block B in the liposome interacting with the liposome.

SEQ ID NO. 3: The Amino acid Sequence of Block D in the liposome interacting with the liposome.

SEQ ID NO. 4: The Amino acid Sequence of Block Cr having the reverse sequence of Block C in the liposome interacting peptide SEQ ID NO. 5: The Amino acid Sequence of Block C in the liposome interacting with the liposome.

SEQ ID NO. 6: The Amino acid Sequence of Block A in the liposome interacting with the liposome.

SEQ ID NO. 7: The Amino acid Sequence of Block Ar having the reverse sequence of Block A in the liposome interacting peptide SEQ ID NO. 8: LBPr1, which is the liposome interacting with the liposome of the present invention SEQ ID NO. 9: LBPr2, which is the liposome interacting with the liposome of the present invention SEQ ID NO. 10: LBPr3, which is the liposome interacting with the liposome of the present invention SEQ ID NO. 11: LBP1, the peptide binds to the liposome at N-terminal SEQ ID NO. 12: The nucleotide sequence of the backbone of cnvK linker

The invention claimed is:

1. A peptide comprising the amino acid sequence of SEQ ID NO: 8.

2. A fusion protein comprising the peptide according claim 1 and a protein of interest at the N-terminal of the peptide.

3. The fusion protein according to claim 2, wherein the peptide comprising the amino acid sequence of SEQ ID NO: 8 is linked with the protein of interest via a linker comprising the amino acid sequence of SEQ ID NO: 13.

4. A construct comprising a nucleic acid sequence encoding the fusion protein according to claim 2.

5. A method for preparing a liposome encapsulating a protein of interest, comprising
   mixing the fusion protein according to claim 2 and a liposome,
   wherein a lipid bilayer of the liposome comprises 30% or more of DOPC.

6. A liposome encapsulating the fusion protein according to claim 2, wherein the liposome comprises 30% or more of DOPC.

7. A construct comprising a nucleic acid sequence encoding the fusion protein according to claim 3.

8. A method for preparing a liposome encapsulating a protein of interest, comprising
   mixing the fusion protein according to claim 3 and a liposome,
   wherein a lipid bilayer of the liposome comprises 30% or more of DOPC.

9. A liposome encapsulating the fusion protein according to claim 3, wherein the liposome comprises 30% or more of DOPC.

* * * * *